(12) United States Patent
Stoessel

(10) Patent No.: US 10,224,493 B2
(45) Date of Patent: Mar. 5, 2019

(54) BORON-CONTAINING COMPOUNDS

(71) Applicant: Merck Patent GmbH, Darmstadt (DE)

(72) Inventor: Philipp Stoessel, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/026,332

(22) PCT Filed: Sep. 19, 2014

(86) PCT No.: PCT/EP2014/002493
§ 371 (c)(1),
(2) Date: Mar. 31, 2016

(87) PCT Pub. No.: WO2015/049030
PCT Pub. Date: Apr. 9, 2015

(65) Prior Publication Data
US 2016/0248015 A1    Aug. 25, 2016

(30) Foreign Application Priority Data

Oct. 2, 2013 (EP) .................................. 13004765

(51) Int. Cl.
| | |
|---|---|
| *C07F 5/02* | (2006.01) |
| *H01L 51/00* | (2006.01) |
| *H05B 33/20* | (2006.01) |
| *C09K 11/02* | (2006.01) |
| *H01L 51/50* | (2006.01) |

(52) U.S. Cl.
CPC .............. *H01L 51/008* (2013.01); *C07F 5/02* (2013.01); *C07F 5/027* (2013.01); *C09K 11/025* (2013.01); *H05B 33/20* (2013.01); *H01L 51/0085* (2013.01); *H01L 51/0087* (2013.01); *H01L 51/5004* (2013.01); *H01L 51/5016* (2013.01); *H01L 51/5072* (2013.01); *H01L 2251/552* (2013.01); *Y02E 10/549* (2013.01)

(58) Field of Classification Search
CPC .......... C07F 5/027; C07F 5/02; H01L 51/008; H01L 51/5004; C09K 11/025
USPC .......................................... 252/519.21; 556/7
See application file for complete search history.

(56) References Cited

U.S. PATENT DOCUMENTS

| | | | | |
|---|---|---|---|---|
| 3,294,763 | A * | 12/1966 | Michaelsen .......... | C07D 307/91 430/75 |
| 6,291,695 | B1 | 9/2001 | Marks et al. | |
| 6,911,551 | B2 | 6/2005 | Stössel et al. | |
| 7,482,067 | B2 * | 1/2009 | Sohn ...................... | B82Y 20/00 252/301.16 |
| 7,737,627 | B2 | 6/2010 | Hwang et al. | |
| 8,927,749 | B2 * | 1/2015 | Boudreault ......... | H01L 51/0094 257/40 |
| 9,871,201 | B2 * | 1/2018 | Pflumm .............. | H01L 51/0056 |
| 2004/0063981 | A1 * | 4/2004 | Stossel ...................... | C07F 5/02 556/170 |
| 2004/0260090 | A1 * | 12/2004 | Treacher ................ | C08G 61/00 544/224 |
| 2006/0241321 | A1 * | 10/2006 | Stossel .................. | H01L 51/008 568/1 |
| 2007/0265473 | A1 * | 11/2007 | Becker .................. | C08G 61/02 568/3 |
| 2008/0113468 | A1 * | 5/2008 | Spreitzer ................ | C08G 61/12 438/99 |
| 2011/0193074 | A1 * | 8/2011 | Lee ....................... | C07D 209/82 257/40 |
| 2014/0316134 | A1 | 10/2014 | Stoessel et al. | |

FOREIGN PATENT DOCUMENTS

| | | |
|---|---|---|
| JP | 2003-261473 A | 9/2003 |
| JP | 2005290000 A | 10/2005 |
| WO | WO-02051850 A1 | 7/2002 |
| WO | WO-2010011426 A1 | 1/2010 |
| WO | WO-2010126233 A1 | 11/2010 |
| WO | WO-2013083216 A1 | 6/2013 |
| WO | WO-2013094951 A1 | 6/2013 |

OTHER PUBLICATIONS

International Search Report, dated Mar. 17, 2015, included in WO 2015/049030.*
Xu, X., et al., "Dimesitylboryl-functionalized fluorene derivatives: Promising luminophors with good electron-transporting ability for deep blue organic light-emitting diodes", Dyes and Pigments, 2014, vol. 101, pp. 136-141.
Charlot, M., et al. "Investigation of two-photon absorption behavior in symmetrical acceptor-π-acceptor derivatives with dimesitylboryl end-groups. Evidence of new engineering routes for TPA/ transparency trade-off optimization", Physical Chemistry Chemical Physics, vol. 7, No. 4, (2005), pp. 600-606.
Chen, Y., et al., "The synthesis and single and two-photon excited fluorescence of a new quasi-quadrupolar organoborane compound", Journal of Molecular Structure, vol. 969, No. 1-3, (2010), pp. 182-186.
International Search Report for PCT/EP2014/002493 dated Mar. 17, 2015.
Makino, T., et al., "Concise Synthesis of Diborylxanthenes", Synthesis 2008, No. 6, (2008), pp. 859-864.
Parab, K., et al., "Synthesis and Characterization of Luminescent Polystyrene Derivatives with Sterically Protected Fluorenyl- and Carbazolylborane Moieties", Macromolecules, vol. 44, No. 15, (2011), pp. 5961-5967.
Zhang, Y., et al., "Theoretical study on the electronic structure and optical properties of carbazole-πt-dimesitylborane as bipolar fluorophores for nondoped blue OLEDs", Journal of Molecular Graphics and Modelling, vol. 34, (2012), pp. 46-56.

* cited by examiner

Primary Examiner — Douglas J McGinty

(57) ABSTRACT

The invention relates to boron-containing compounds with bicyclic structural units and to electronic devices, in particular organic electroluminescent devices, containing said compounds.

24 Claims, No Drawings

BORON-CONTAINING COMPOUNDS

CROSS-REFERENCE TO RELATED APPLICATIONS

This application is a national stage application (under 35 U.S.C. § 371) of PCT/EP2014/002493, filed Sep. 16, 2014, which claims benefit of European Application No. 13004765.7, filed Oct. 2, 2013, both of which are incorporated herein by reference in their entirety.

The present invention relates to boron-containing compounds suitable for use in electronic devices. The present invention further relates to processes for preparation thereof and to electronic devices.

BACKGROUND OF THE INVENTION

Electronic devices containing organic, organometallic and/or polymeric semiconductors are becoming increasingly important, and are being used in many commercial products for reasons of cost and because of their performance. Examples here include organic-based charge transport materials (for example triarylamine-based hole transporters) in photocopiers, organic or polymeric light-emitting diodes (OLEDs or PLEDs) and in readout and display devices or organic photoreceptors in photocopiers. Organic solar cells (O-SCs), organic field-effect transistors (O-FETs), organic thin-film transistors (O-TFTs), organic integrated circuits (O-ICs), organic optical amplifiers and organic laser diodes (O-lasers) are at an advanced stage of development and may have great future significance.

Many of these electronic devices, irrespective of the respective end use, have the following general layer structure which can be adjusted for the particular application:
(1) substrate,
(2) electrode, frequently metallic or inorganic, but also composed of organic or polymeric conductive materials,
(3) charge injection layer(s) or interlayer(s), for example to compensate for unevenness in the electrode ("planarization layer"), frequently composed of a conductive doped polymer,
(4) organic semiconductors,
(5) possibly further charge transport, charge injection or charge blocker layers,
(6) counterelectrode, materials as specified in (2),
(7) encapsulation.

The above arrangement is the general structure of an organic electronic device, it being possible to combine various layers, such that the result in the simplest case is an arrangement composed of two electrodes with an organic layer in between. In this case, the organic layer fulfills all functions including the emission of light in the case of OLEDs. A system of this kind is described, for example, in WO 90/13148 A1, based on poly(p-phenylenes).

Electronic devices comprising boron-containing compounds are described inter alia in publications WO 02/052661 A1 and WO 02/051850 A1. The fluorene or spiro compounds detailed explicitly therein are substituted by boron-containing radicals at the 2,7 positions or at 2',7' positions of the rings.

Known electronic devices have a useful profile of properties. However, there is a constant need to improve the properties of these devices.

These properties especially include the energy efficiency with which an electronic device solves the problem defined. In the case of organic light-emitting diodes, which may be based either on low molecular weight compounds or on polymeric materials, the light yield in particular should be sufficiently high that a minimum amount of electrical power has to be applied to achieve a particular luminous flux. In addition, a minimum voltage should also be necessary to achieve a defined luminance. A further particular problem is the lifetime of the electronic devices.

BRIEF SUMMARY OF THE INVENTION

It is therefore an object of the present invention to provide novel compounds which lead to electronic devices having improved properties. It is a particular object to provide hole blocker materials, electron injection materials and/or electron transport materials which exhibit improved properties in relation to efficiency, operating voltage and/or lifetime.

Moreover, the compounds should be processible in a very simple manner, and especially exhibit good solubility and film formation.

A further object can be considered that of providing electronic devices having excellent performance very inexpensively and in constant quality. Furthermore, it should be possible to use or adapt the electronic devices for many purposes. More particularly, the performance of the electronic devices should be maintained over a broad temperature range.

It has been found that, surprisingly, these objects and others which are not specified explicitly but can be inferred or discerned directly from the connections discussed herein by way of introduction are achieved by compounds having all the features of claim 1. Appropriate modifications to the compounds of the invention are protected in the dependent claims that refer back to claim 1.

DETAILED DESCRIPTION OF THE INVENTION

The invention thus provides a boron-containing compound comprising at least one structure of the formulae (I) and/or (II)

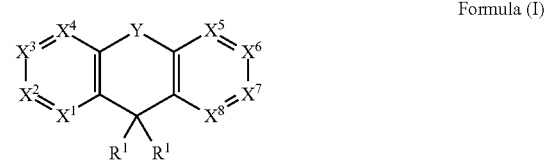

Formula (I)

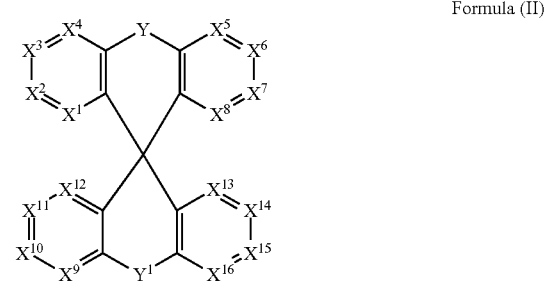

Formula (II)

where the symbols used are as follows:
$X^1, X^2, X^3, X^4, X^5, X^6, X^7, X^8, X^9, X^{10}, X^{11}, X^{12}, X^{13}, X^{14}, X^{15}, X^{16}$ is the same or different at each instance and is N, $CR^2$ or C—Z, where at least one of the $X^1, X^2, X^3, X^4, X^5, X^6, X^7, X^8, X^9, X^{10}, X^{11}, X^{12}, X^{13}, X^{14}, X^{15}, X^{16}$ groups is C—Z and no two adjacent $X^1$, $X^2$, $X^3$, $X^4$, $X^5$, $X^6$, $X^7$, $X^8$, $X^9$, $X^{10}$, $X^{11}$, $X^{12}$, $X^3$, $X^{14}$, $X^{15}$, $X^{16}$ groups are simultaneously N;

Y, $Y^1$ is the same or different at each instance and is a bond or a bivalent bridge selected from $BR^3$, O, S, $C(R^3)_2$, $C(R^3)=C(R^3)$, $N(R^3)$, $Si(R^3)_2$, C=O, C=$C(R^3)_2$, S=O, $SO_2$, $C(R^3)_2$—$C(R^3)_2$, and 1,2-phenylene, preferably from O, S, $C(R^3)_2$, $C(R^3)=C(R^3)$, $N(R^3)$, $Si(R^3)_2$, C=O, C=$C(R^3)_2$, S=O, $SO_2$, $C(R^3)_2$—$C(R^3)_2$, and 1,2-phenylene;

$R^1$, $R^2$, $R^3$
is the same or different at each instance and is H, D, F, Cl, Br, I, CHO, C(=O)$Ar^1$, P(=O)$(Ar^1)_2$, S(=O)$Ar^1$, $S(=O)_2Ar^1$, CN, $NO_2$, $Si(R^4)_3$, $B(OR^4)_2$, $OSO_2R^4$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^4$ radicals, where one or more nonadjacent $CH_2$ groups may be replaced by $R^4C=CR^4$, C≡C, $Si(R^4)_2$, $Ge(R^4)_2$, $Sn(R^4)_2$, C=O, C=S, C=Se, P(=O)$(R^4)$, SO, $SO_2$, O, S or $CONR^4$ and where one or more hydrogen atoms may be replaced by D, F, Cl, Br, I, CN or $NO_2$, or an aromatic or heteroaromatic ring system which has 5 to 40 aromatic ring atoms, each of which may be substituted by one or more $R^4$ radicals, or an aryloxy or heteroaryloxy group which has 5 to 40 aromatic ring atoms and may be substituted by one or more $R^4$ radicals, or a diarylamino, diheteroarylamino or arylheteroarylamino group, or a combination of these systems; at the same time, two or more adjacent $R^1$, $R^2$ or $R^3$ substituents may also form a mono- or polycyclic, aliphatic or aromatic ring system with one another;

$R^4$ is the same or different at each instance and is H, D, F, Cl, Br, I, CHO, C(=O)$Ar^1$, P(=O)$(Ar^1)_2$, S(=O)$Ar^1$, $S(=O)_2Ar^1$, CN, $NO_2$, $Si(R^5)_3$, $B(OR^5)_2$, $OSO_2R^5$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^5$ radicals, where one or more nonadjacent $CH_2$ groups may be replaced by C=C, $Si(R^5)_2$, $Ge(R^5)_2$, $Sn(R^5)_2$, C=O, C=S, C=Se, P(=O)$(R^5)$, SO, $SO_2$, O, S or $CONR^5$ and where one or more hydrogen atoms may be replaced by D, F, Cl, Br, I, CN or $NO_2$, or a combination of these systems; at the same time, two or more adjacent $R^4$ substituents may also form a mono- or polycyclic, aliphatic or aromatic ring system with one another;

$Ar^1$ is the same or different at each instance and is an aromatic or heteroaromatic ring system which has 5 to 30 aromatic ring atoms and may be substituted by one or more $R^3$ radicals; at the same time, it is also possible for two $Ar^1$ radicals bonded to the same phosphorus atom to be joined to one another by a single bond or a bridge selected from $B(R^5)$, $C(R^5)_2$, $Si(R^5)_2$, C=O, C=$NR^5$, C=$C(R^5)_2$, O, S, S=O, $SO_2$, $N(R^5)$, $P(R^5)$ and P(=O)$R^5$;

$R^5$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more adjacent $R^5$ substituents together may also form a mono- or polycyclic, aliphatic or aromatic ring system;

Z is a group of the formula (III)

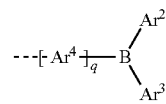

Formula (III)

in which the symbols used are as follows;

$Ar^2$, $Ar^3$
is the same or different at each instance and is an aromatic or heteroaromatic ring system which has 5 to 30 aromatic ring atoms and may be substituted by one or more $R^3$ radicals; at the same time, it is also possible for the $Ar^2$ and $Ar^3$ radicals to be joined to one another by a single bond or a bridge selected from $B(R^5)$, $C(R^5)_2$, $Si(R^5)_2$, C=O, C=$NR^5$, C=$C(R^5)_2$, O, S, S=O, $SO_2$, $N(R^5)$, $P(R^5)$ and P(=O)$R^5$;

q is 0 or 1; and $Ar^4$ is the same or different at each instance and is an aryl group having 6 to 40 carbon atoms or a heteroaryl group having 3 to 40 carbon atoms, each of which may be substituted by one or more $R^3$ radicals; where the dashed line represents the bond of the Z group to the carbon atom of the aromatic or heteroaromatic ring, with the proviso that
if both Y and $Y^1$ are a bond, $X^2$ and $X^7$ may not simultaneously be a group of the formula C—Z nor may $X^{11}$ and $X^{14}$ simultaneously be a group of the formula C—Z.

The above definition of the $X^1$ to $X^{16}$ groups means that both the compound of the formula (I) and the compound of the formula (II) contain at least one group of the formula (III), meaning that the compounds always contain at least one boron atom.

In this context, "adjacent carbon atoms" means that the carbon atoms are bonded directly to one another. In addition, "adjacent radicals" in the definition of the radicals means that these radicals are bonded to the same carbon atom or to adjacent carbon atoms. These definitions apply correspondingly, inter alia, to the terms "adjacent groups" and "adjacent substituents".

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 60 carbon atoms in the ring system. A heteroaromatic ring system in the context of this invention contains 1 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. are also to be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl or terphenyl, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$- to $C_{40}$-alkyl group in which individual hydrogen atoms or $CH_2$ groups may also be replaced by the abovementioned groups are understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5-60 aromatic ring atoms and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, triphenyl, triphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preference is given to compounds comprising structures of the formula (I) and/or (II), which are characterized in that not more than eight, preferably not more than four and more preferably not more than two of the $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$ groups are N. Most preferably, all the $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$ groups are $CR^2$ or C—Z. In this connection, it should be emphasized that the $CR^2$ groups differ from the C—Z groups.

Preference is further given to compounds in which, if Y is a bond, $X^2$ and $X^7$ are not a group of the formula C—Z. More preferably, the $X^2$ and $X^7$ groups are a group of the formula $CR^2$, preferably C—H, if Y is a bond. If $Y^1$ is a bond, preference is given to compounds in which $X^{11}$ and $X^{14}$ are not a group of the formula C—Z. More preferably, the $X^{11}$ and $X^{14}$ groups are a group of the formula $CR^2$, preferably C—H, if $Y^1$ is a bond.

It may additionally be the case that not more than six, preferably not more than four and more preferably not more than two of the $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$ and $X^{16}$ groups are C—Z. More preferably, exactly one of the $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$ and $X^{16}$ groups is C—Z.

Preference is further given to compounds of formula (I) in which at least one of the $X^1$, $X^4$, $X^5$ and $X^8$ groups, more preferably exactly one of the $X^1$, $X^4$, $X^5$ and $X^8$ groups, is C—Z. It may preferably additionally be the case that, in formula (II), at least one of the $X^1$, $X^4$, $X^5$, $X^8$, $X^9$, $X^{12}$, $X^{13}$ and $X^{16}$ groups, more preferably exactly one of the $X^1$, $X^4$, $X^5$, $X^8$, $X^9$, $X^{12}$, $X^{13}$ and $X^{16}$ groups, is C—Z.

Preference is additionally given to compounds having the feature that, in formula (I), at least 4 of the $X^1$, $X^2$, $X^3$, $X^4$, $X^5$, $X^6$, $X^7$ and $X^8$ groups are C—H and/or, in formula (II), at least 8 and preferably at least 12 of the $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, and $X^{16}$ groups are C—H.

In a further configuration of the present invention, preference is given to compounds in which the $X^5$, $X^6$, $X^7$, $X^8$, $X^9$, $X^{10}$, $X^{11}$ and $X^{12}$ groups are $CR^2$.

Preference is further given to compounds in which at least two and preferably at least three of the $X^2$, $X^7$, $X^{11}$ and $X^{14}$ groups are a group of the formula $CR^2$, more preferably C—H. More preferably, all the $X^2$, $X^7$, $X^{11}$ and $X^{14}$ groups may be a group of the formula $CR^2$, more preferably C—H. In a particularly preferred embodiment, $X^2$ is C—Z and $X^7$ is C—H. Further preferably, $X^{11}$ may be C—Z and $X^{14}$ may be C—H, it being especially preferable in this case that $X^2$ is C—Z and $X^7$ is C—H.

In addition, it may be the case that q in formula (I) and/or (II) is 0, such that the boron atom of the Z radical is bonded directly to the fluorene or spiro group.

In a particular aspect of the present invention, compounds of formula (I) differ from compounds of formula (II). It may more preferably be the case that the $R^1$ radicals in formula (I) are not joined to one another.

Preferably, the compound having structures of formula (I) may comprise $R^1$ radicals in which these $R^1$ radicals are the same or different at each instance and are preferably selected from the group consisting of H, D, F, Br, I, CN, $Si(R^4)_3$, $B(OR^4)_2$, $C(=O)Ar^1$, a straight-chain alkyl group having 1 to 10 carbon atoms or a straight-chain alkoxy group having 1 to 10 carbon atoms or an alkenyl group having 2 to 10 carbon atoms or a branched or cyclic alkoxy group having 3 to 10 carbon atoms or a branched or cyclic alkyl group having 3 to 10 carbon atoms, each of which may be substituted by one or more $R^4$ radicals, where one or more hydrogen atoms may be replaced by D or F, or an aromatic or heteroaromatic ring system which has 5 to 30 aromatic ring atoms and may be substituted in each case by one or more $R^4$ radicals; at the same time, two adjacent $R^1$ radicals together or $R^1$ radicals together with $R^4$ radicals may also form a mono- or polycyclic, aliphatic or aromatic ring system. More preferably, these $R^1$ radicals are the same or different at each instance and are selected from the group consisting of H, D, F, a straight-alkoxy group having 1 to 6 carbon atoms or a branched or cyclic alkoxy group having 3 to 10 carbon atoms, a straight-chain alkyl group having 1 to 6 carbon atoms or a branched or cyclic alkyl group having 3 to 10 carbon atoms, where one or more hydrogen atoms may be replaced by D or F, or an aromatic or heteroaromatic ring system which has 5 to 24 aromatic ring atoms and may be substituted in each case by one or more $R^4$ radicals; at the same time, two adjacent $R^1$ radicals together or $R^1$ radicals together with $R^4$ radicals may also form a mono- or polycyclic, aliphatic or aromatic ring system. More preferably, at least one and preferably both of the $R^1$ radicals in formula (I) may be an alkyl radical having 1 to 10 carbon atoms or an aryl group having 6 to 10 carbon atoms, which may be substituted by up to three $R^4$ radicals, where the $R^1$ radicals are more preferably not joined to one another.

When $R^2$ radicals are bonded within the structure of the formula (I) and/or formula (II), these $R^2$ radicals are the same or different at each instance and are preferably selected from the group consisting of H, D, F, Br, I, CN, $Si(R^4)_3$, $B(OR^4)_2$, $C(=O)Ar^1$, a straight-chain alkyl group having 1 to 10 carbon atoms or a straight-chain alkoxy group having 1 to 10 carbon atoms an alkenyl group having 2 to 10 carbon atoms or a branched or cyclic alkoxy group having 3 to 10 carbon atoms or a branched or cyclic alkyl group having 3 to 10 carbon atoms, each of which may be substituted by one or more $R^4$ radicals, where one or more hydrogen atoms may be replaced by D or F, or an aromatic or heteroaromatic ring system which has 5 to 30 aromatic ring atoms and may be substituted in each case by one or more $R^4$ radicals; at the same time, two adjacent $R^2$ radicals together or $R^2$ radicals together with $R^4$ radicals may also form a mono- or polycyclic, aliphatic or aromatic ring system. More preferably, these R radicals are the same or different at each instance and are selected from the group consisting of H, D, F, a straight-chain alkoxy group having 1 to 6 carbon atoms or a branched or cyclic alkoxy group having 3 to 10 carbon atoms, a straight-chain alkyl group having 1 to 6 carbon atoms or a branched or cyclic alkyl group having 3 to 10 carbon atoms, where one or more hydrogen atoms may be replaced by D or F, or an aromatic or heteroaromatic ring system which has 5 to 24 aromatic ring atoms and may be substituted in each case by one or more $R^4$ radicals; at the same time, two adjacent $R^2$ radicals together or $R^2$ radicals together with $R^4$ radicals may also form a mono- or polycyclic, aliphatic or aromatic ring system.

It may additionally be the case that the $Ar^2$ and $Ar^3$ radicals are an aryl group which has 6 to 10 carbon atoms, preferably 6 carbon atoms, and may be substituted by up to three $R^3$ radicals; at the same time, it is also possible for the $Ar^2$ and $Ar^3$ radicals to be joined to one another by a single bond or a bridge selected from $B(R^5)$, $C(R^5)_2$, $Si(R^5)_2$, $C=O$, $C=NR^5$, $C=C(R^5)_2$, O, S, $S=O$, $SO_2$, $N(R^5)$, $P(R^5)$ and $P(=O)R^5$. In a particular aspect, the $Ar^2$ and $Ar^3$ radicals are an aryl group which has 6 carbon atoms and may be substituted by up to 3 alkyl radicals having 1 to 4 carbon atoms, preferably by methyl radicals. In a further aspect, the $Ar^2$ and $Ar^3$ radicals are an aryl group which has 6 carbon atoms and may be substituted by up to 2 aryl radicals having 6 to 10 carbon atoms, preferably by phenyl radicals, where the aryl radicals may preferably be joined to one another via a bond.

It may additionally be the case that the compound comprises structures of the formulae (IV) and/or (V)

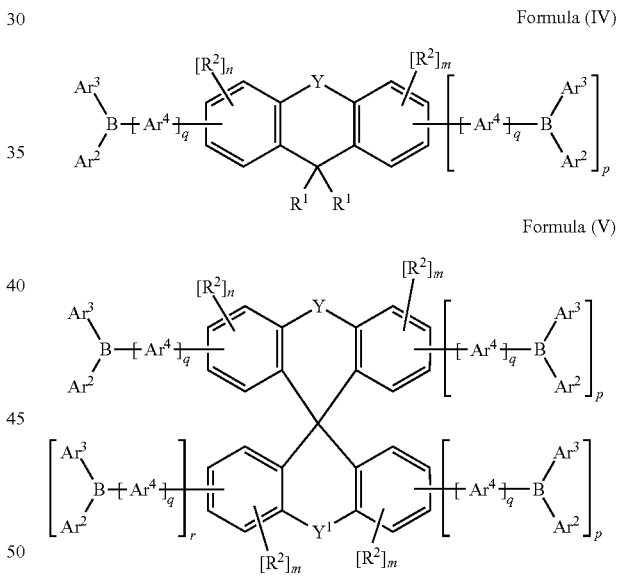

Formula (IV)

Formula (V)

where the symbols used have the definitions given above and n, m, p, q, r are the same or different at each instance and are 0 or 1.

In compounds having structures of formula (IV), Y may preferably be a bond, O, S, $C=O$ or $N(R^3)$, preferably a bond, O or $N(Ar^1)$, especially preferably a bond, where the symbols used have the definitions given above.

For compounds having structures of formula (V), it may preferably be the case that Y is O or a bond and $Y^1$ is a bond, O, S, $C=O$ or $N(R^3)$, preferably a bond, O or $N(Ar^1)$, where the symbols used have the definitions given above. In a particular aspect, it may be a feature of compounds having structures of formula (V) that Y is O and $Y^1$ is a bond, O, S, $C=O$ or $N(R^3)$. More preferably, in compounds having structures of formula (V), Y is a bond and $Y^1$ is a bond, O, S, C=O or N(R³), especially preferably a bond. It may more preferably be the case that the compound comprises structures of the formulae (IV-1) and/or (IV-2)

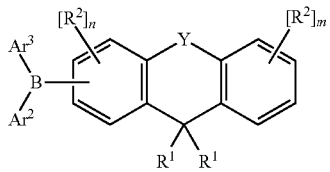

Formula (IV-1)

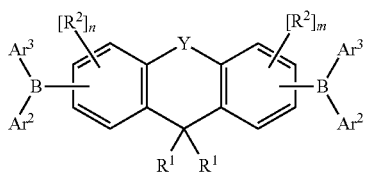

Formula (IV-2)

where the symbols used have the definitions given above and n, m are the same or different at each instance and are 0 or 1.

Preferably, for compounds having structures of formula (IV-1) or formula (IV-2), the Y group may be O, N(Ar¹) or a bond, preferably O or a bond, especially preferably a bond.

Preferably, the $R^1$ radicals in conjunction with structures of formula (IV-1) or (IV-2) may be the same or different at each instance and may preferably be selected from the group consisting of H, D, F, Br, I, CN, Si(R⁴)₃, B(OR⁴)₂, C(=O)Ar¹, a straight-chain alkyl group having 1 to 10 carbon atoms or a straight-chain alkoxy group having 1 to 10 carbon atoms or an alkenyl group having 2 to 10 carbon atoms or a branched or cyclic alkoxy group having 3 to 10 carbon atoms or a branched or cyclic alkyl group having 3 to 10 carbon atoms, each of which may be substituted by one or more R⁴ radicals, where one or more hydrogen atoms may be replaced by D or F, or an aromatic or heteroaromatic ring system which has 5 to 30 aromatic ring atoms and may be substituted in each case by one or more R⁴ radicals; at the same time, two adjacent R¹ radicals together or R¹ radicals together with R⁴ radicals may also form a mono- or polycyclic, aliphatic or aromatic ring system. More preferably, these R¹ radicals in conjunction with structures of formula (IV-1) or (IV-2) are the same or different at each instance and are selected from the group consisting of H, D, F, N a straight-chain alkoxy group having 1 to 6 carbon atoms or a branched or cyclic alkoxy group having 3 to 10 carbon atoms, a straight-chain alkyl group having 1 to 6 carbon atoms or a branched or cyclic alkyl group having 3 to 10 carbon atoms, where one or more hydrogen atoms may be replaced by D or F, or an aromatic or heteroaromatic ring system which has 5 to 24 aromatic ring atoms and may be substituted in each case by one or more R⁴ radicals; at the same time, two adjacent R¹ radicals together or R¹ radicals together with R⁴ radicals may also form a mono- or polycyclic, aliphatic or aromatic ring system. More preferably, at least one and preferably both of the R¹ radicals in formula (IV-1) or (IV-2) may be an alkyl radical having 1 to 10 carbon atoms or an aryl group having 6 to 10 carbon atoms, which may be substituted by up to three R⁴ radicals, where the R¹ radicals are more preferably not joined to one another.

Preference is further given to compounds comprising the structures of the formulae (IV-3), (IV-4) and/or (IV-5)

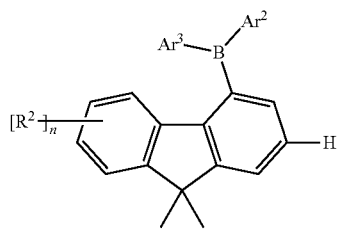

Formula (IV-3)

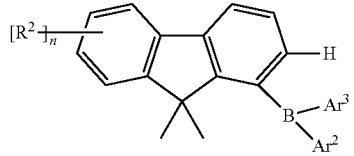

Formula (IV-4)

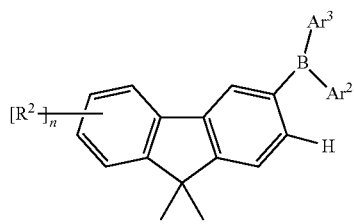

Formula (IV-5)

where the symbols used have the definitions given above and n is 0 or 1.

Preference is further given to compounds comprising structures of the formulae (IV-6), (IV-7) and/or (IV-8)

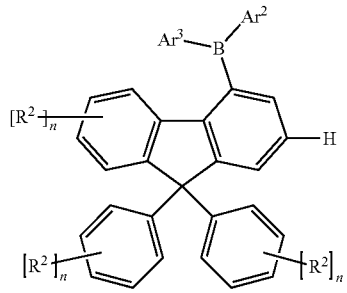

Formula (IV-6)

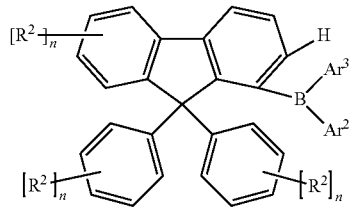

Formula (IV-7)

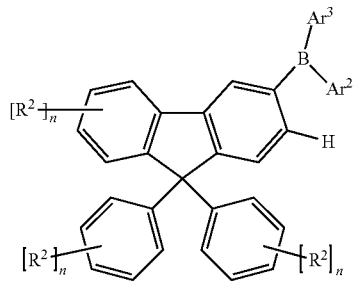

Formula (IV-8)

where the symbols used have the definitions given above and n is the same or different at each instance and is 0 or 1.

It may more preferably be the case that the compound comprises structures of the formula (V-1), (V-2), (V-3) and/or (V-4)

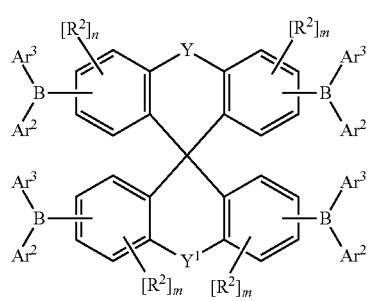
Formula (V-1)

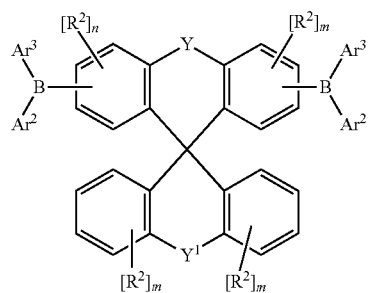
Formula (V-2)

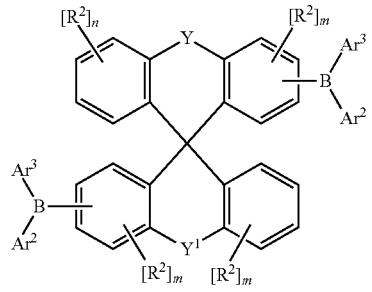
Formula (V-3)

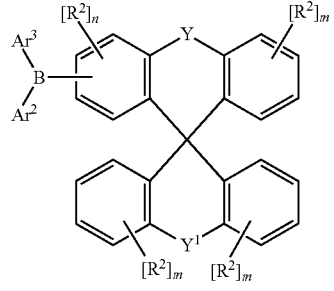
Formula (V-4)

where the symbols used have the definitions given above and n, m are the same or different at each instance and are 0 or 1.

For compounds having structures of one of the formulae (V-1), (V-2), (V-3) or (V-4), it may preferably be the case that Y is O or a bond and Y is a bond, O, S, C=O or N($R^3$), preferably a bond, O or N($Ar^1$), where the symbols used have the definitions given above.

Preference is further given to compounds comprising structures of the formulae (V-5), (V-6), (V-7), (V-8), (V-9) and/or (V-10)

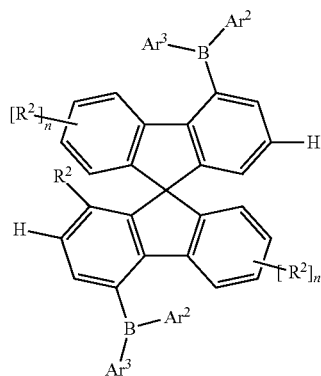
Formula (V-5)

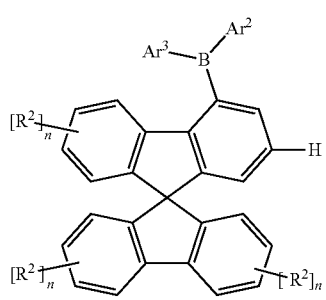
Formula (V-6)

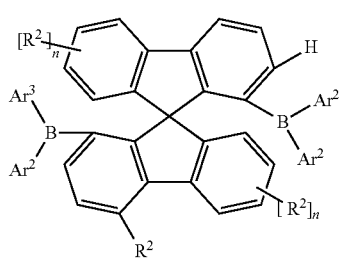
Formula (V-7)

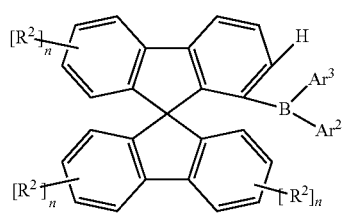
Formula (V-8)

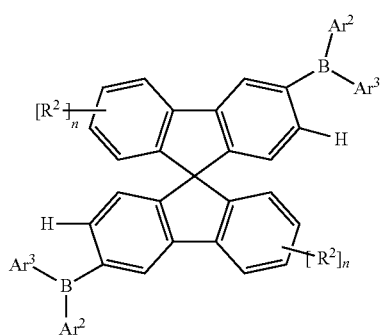
Formula (V-9)

-continued

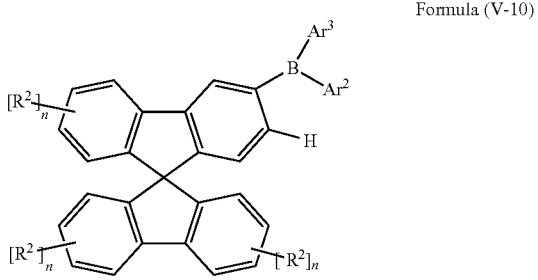

Formula (V-10)

where the symbols used have the definitions given above and n is the same or different at each instance and is 0 or 1.

More particularly, the compounds of the invention have a much higher T1 level compared to prior art compounds, this being advantageous for the construction of green and especially of blue phosphorescent OLEDs. This advantage is essential especially for the use of the materials as triplet matrix material (TMM), hole blocker material (HBM) and electron transport material (ETM). In the emitting layer and the adjoining layers (EBM/ETM), the T1 level of TMM, EBH, ETM should be higher than or equal to that of the emitting material, in order to avoid quenching of the emission.

Molecular orbitals, especially also the highest occupied molecular orbital (HOMO) and the lowest unoccupied molecular orbital (LUMO), the energy levels thereof and the energy of the lowest triplet state $T_1$ and that of the lowest excited singlet state $S_1$ of the materials are determined via quantum-chemical calculations. For calculation of organic substances without metals, an optimization of geometry is first conducted by the "Ground State/Semi-empirical/Default Spin/AM1/Charge 0/Spin Singlet" method. Subsequently, an energy calculation is effected on the basis of the optimized geometry. This is done using the "TD-SCF/DFT/Default Spin/B3PW91" method with the "6-31G(d)" basis set (charge 0, spin singlet). For metal-containing compounds, the geometry is optimized via the "Ground State/Hartree-Fock/Default Spin/LanL2 MB/Charge 0/Spin Singlet" method. The energy calculation is effected analogously to the above-described method for the organic substances, except that the "LanL2DZ" basis set is used for the metal atom and the "6-31G(d)" basis set for the ligands. The HOMO energy level HEh or LUMO energy level LEh is obtained from the energy calculation in Hartree units. This is used to determine the HOMO and LUMO energy levels in electron volts, calibrated by cyclic voltammetry measurements, as follows:

HOMO(eV)=((HEh*27.212)−0.9899)/1.1206

LUMO(eV)=((LEh*27.212)−2.0041)/1.385

These values are to be regarded as HOMO and LUMO energy levels of the materials in the context of this application.

The lowest triplet state $T_1$ is defined as the energy of the triplet state having the lowest energy, which is apparent from the quantum-chemical calculation described.

The lowest excited singlet state $S_1$ is defined as the energy of the excited singlet state having the lowest energy, which is apparent from the quantum-chemical calculation described.

The method described herein is independent of the software package used and always gives the same results. Examples of frequently utilized programs for this purpose are "Gaussian09 W" (Gaussian Inc.) and Q-Chem 4.1 (Q-Chem, Inc.).

The boron-containing compounds of the invention comprising structures of the formula (I) and/or (II) may also be chiral according to the structure. This is the case especially when they contain substituents, for example alkyl, alkoxy or aralkyl groups, having one or more stereocenters. Since the base structure of the boron-containing compound may also be a chiral structure, the formation of diastereomers and multiple pairs of enantiomers is possible. In that case, the compounds of the invention include both the mixtures of the different diastereomers or the corresponding racemates and the individual isolated diastereomers or enantiomers.

Preferably, the compound may be in the form of an enantiomer mixture, more preferably of a diastereomer mixture. As a result, it is unexpectedly possible to enhance the properties of electronic devices obtainable using the compounds of the invention. These properties especially include the lifetime of the devices.

Particularly preferred compounds include structures according to the following formulae 1 to 40:

1

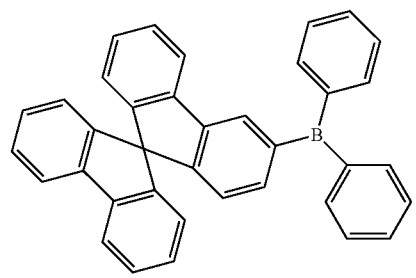

2

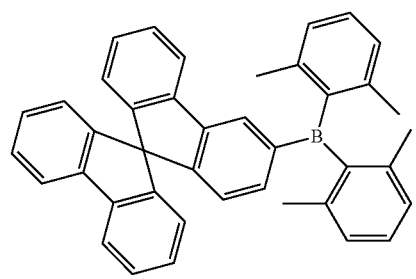

3

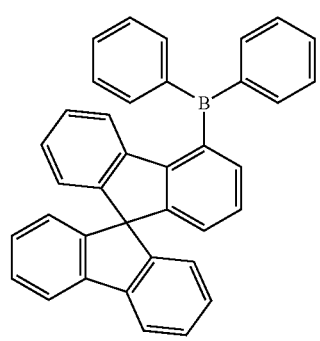

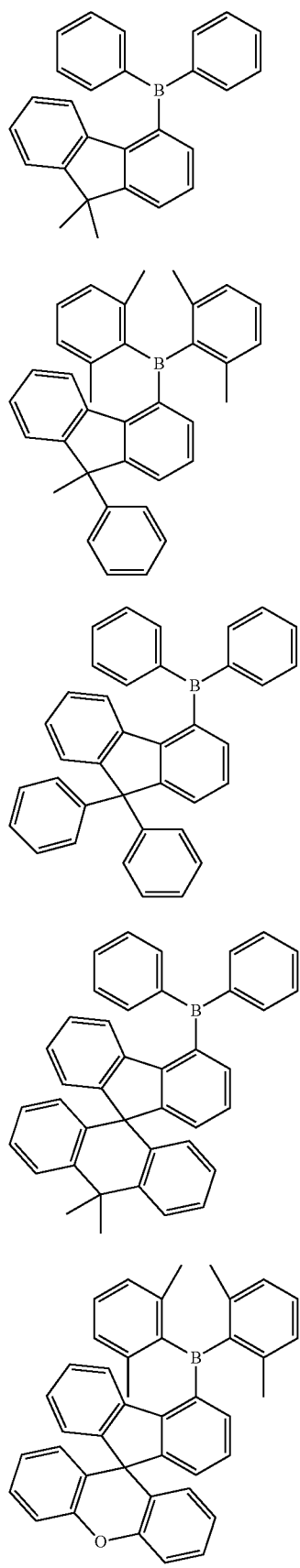
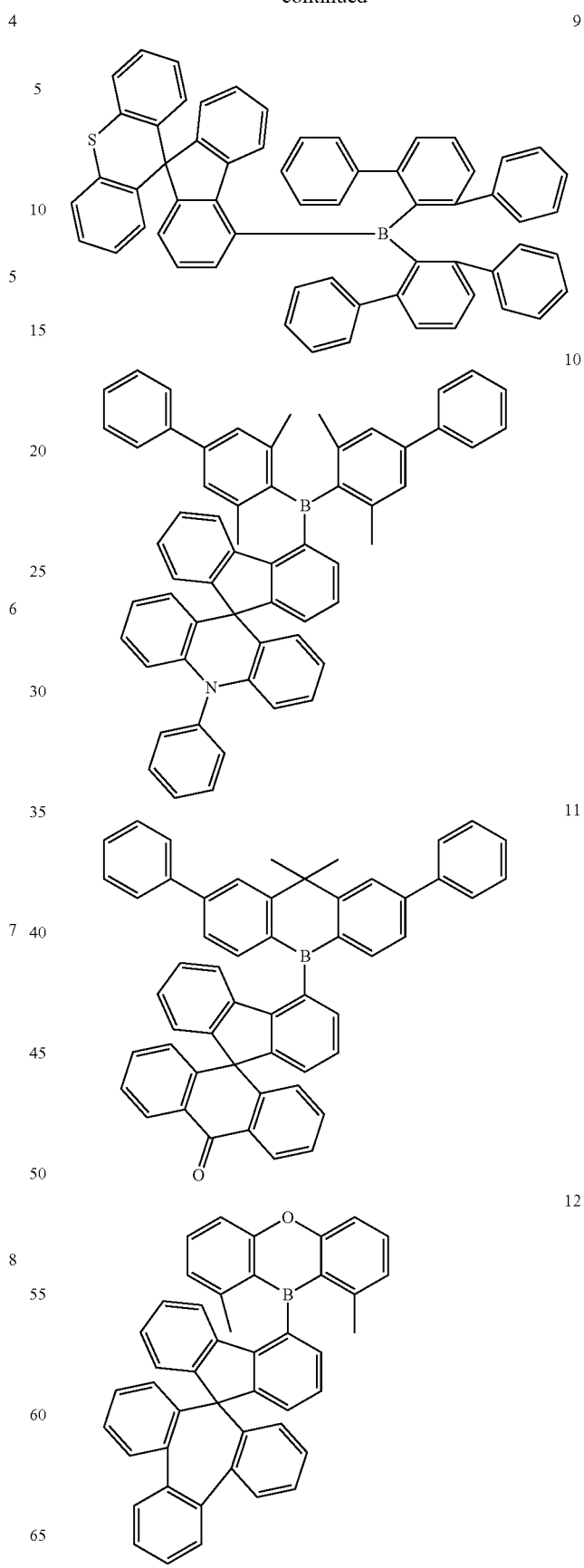

13
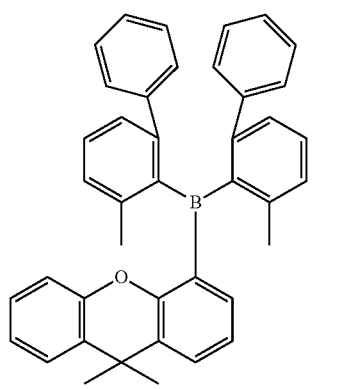
14
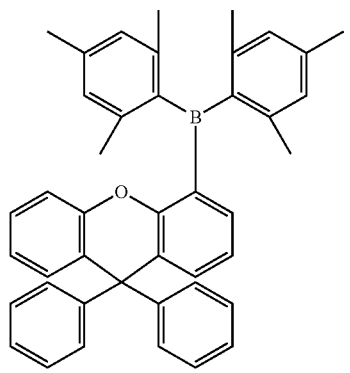
15
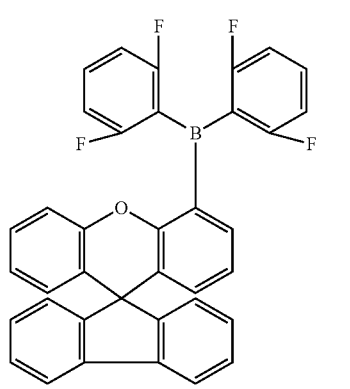
16
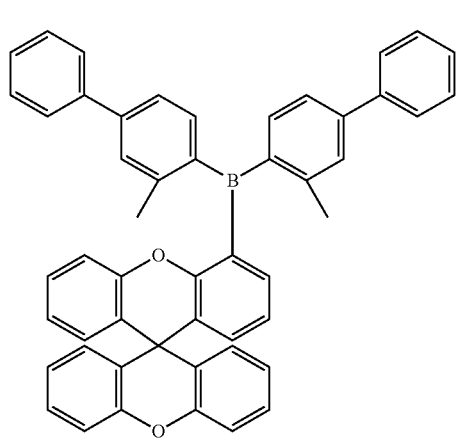
17
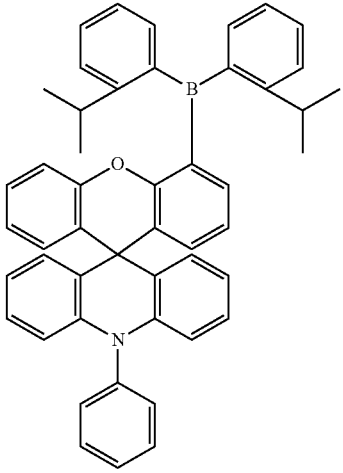
18
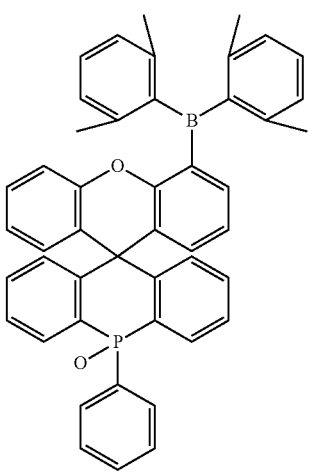
19
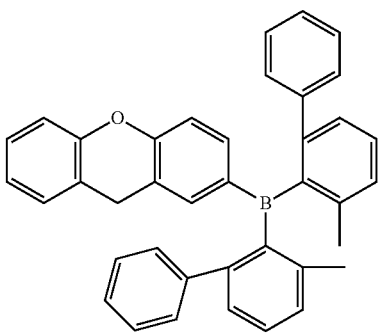
20
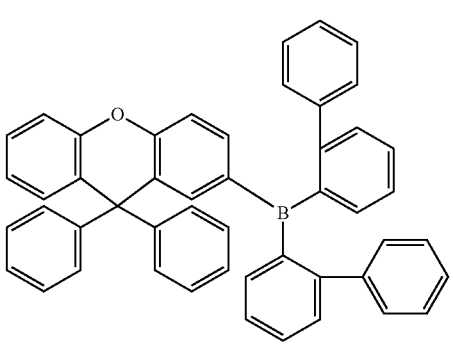

21
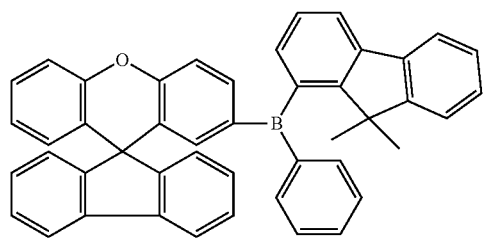
22
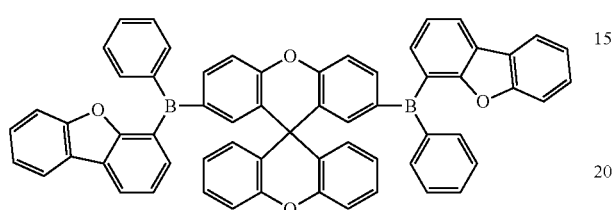
23
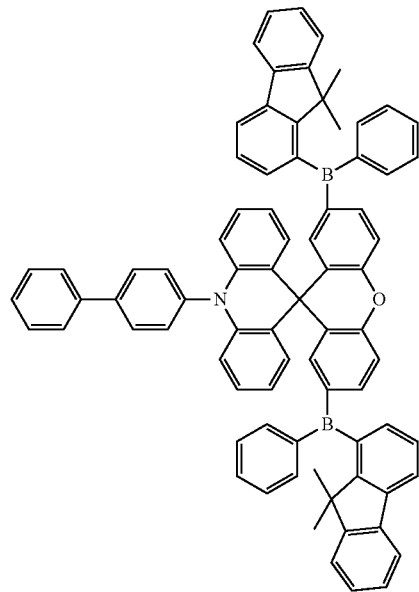
24
25
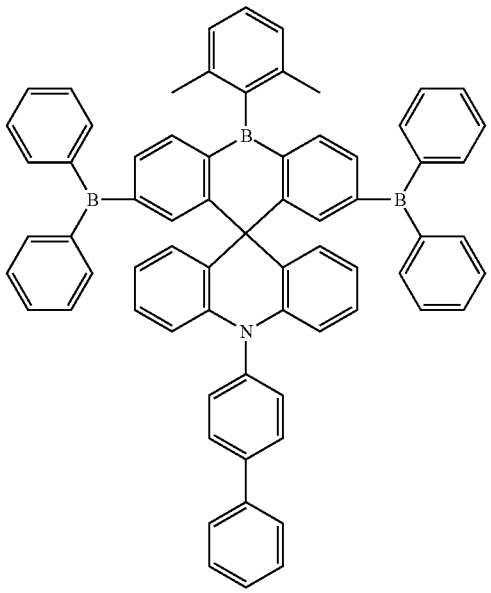
26
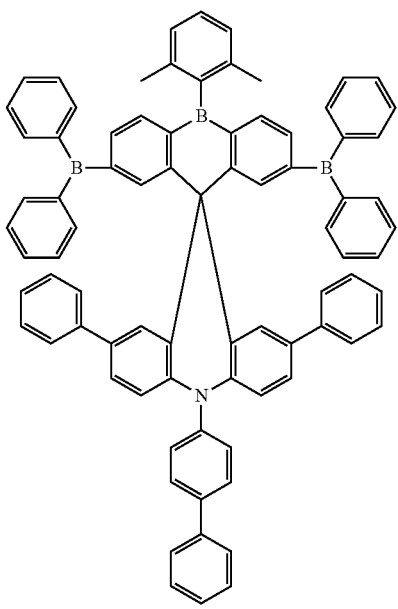

27
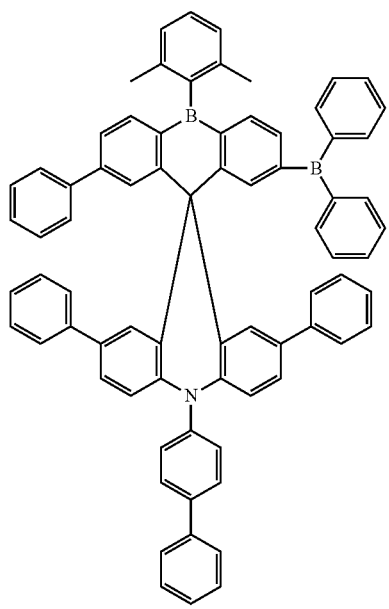
28
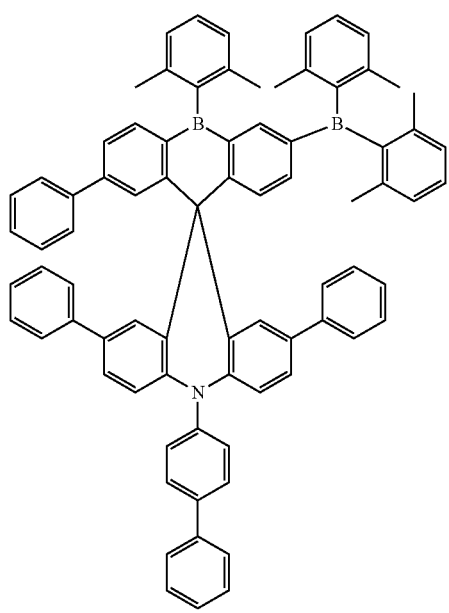
29
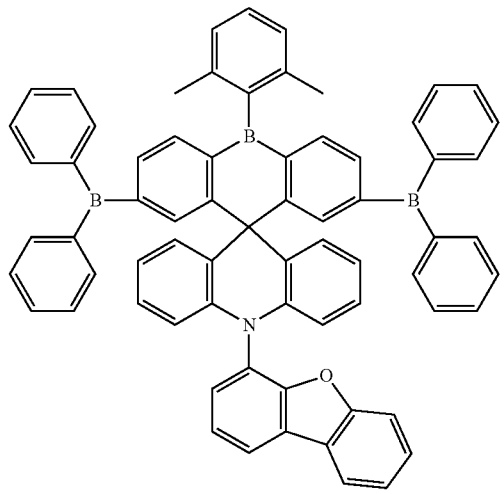
30
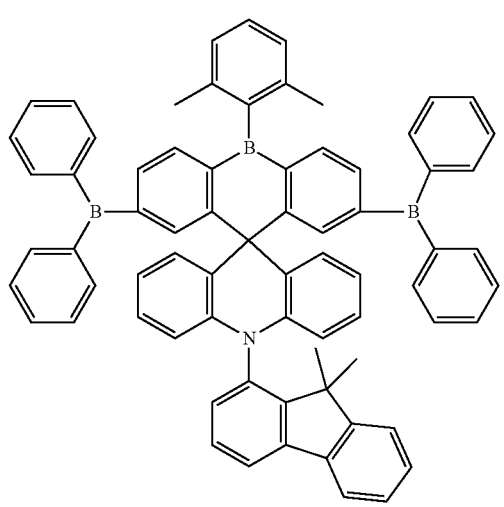
31
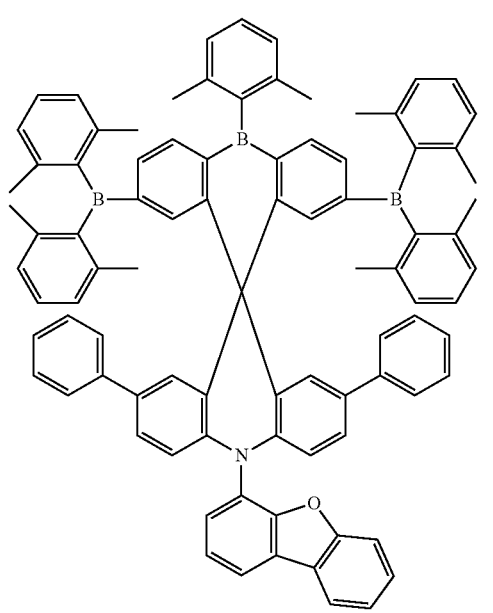

32
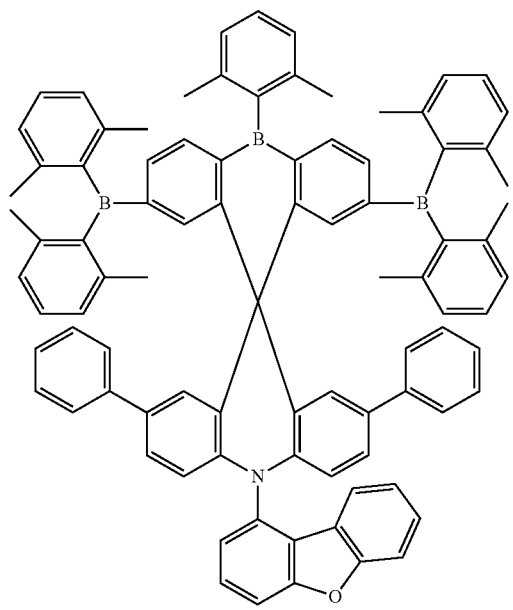
33
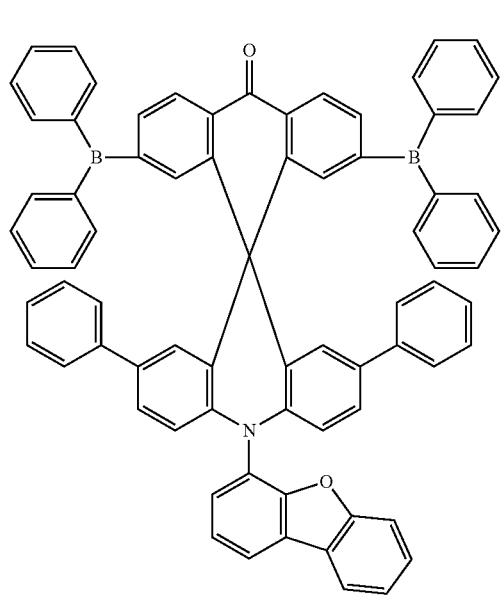
34
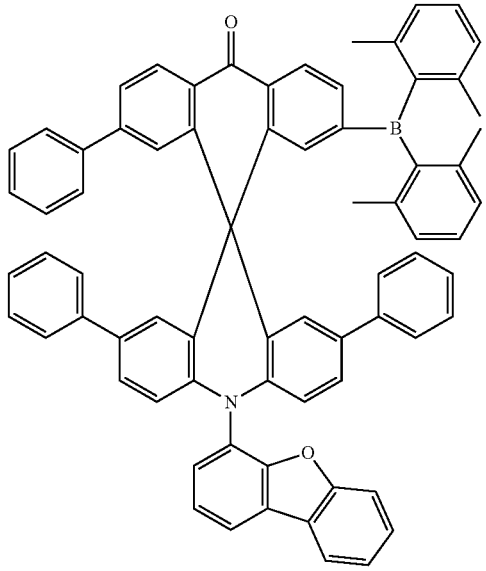
35
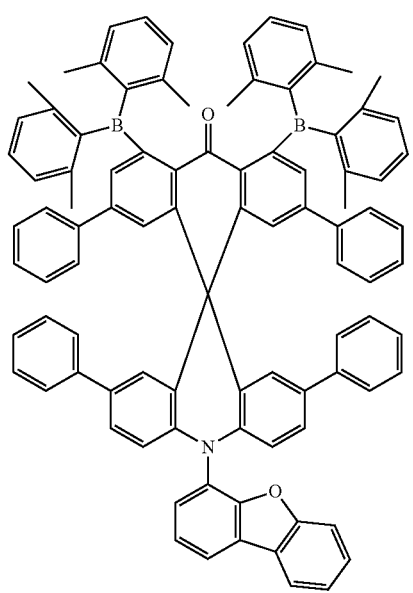

36
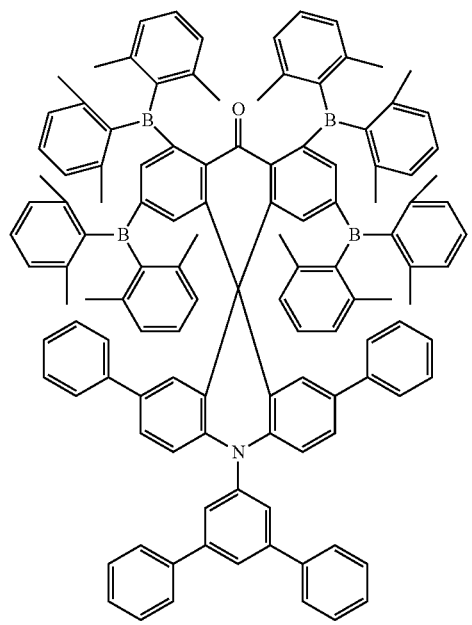
37
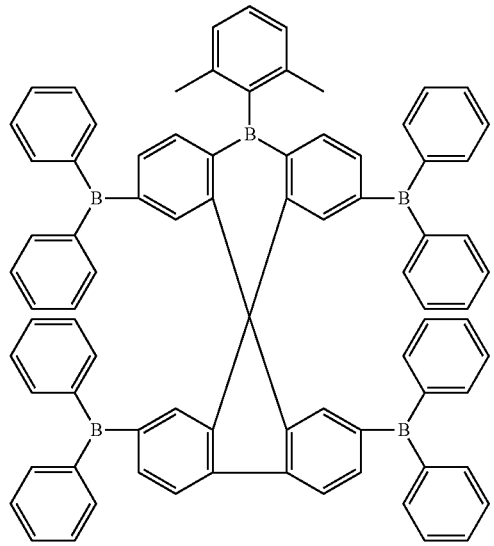
38
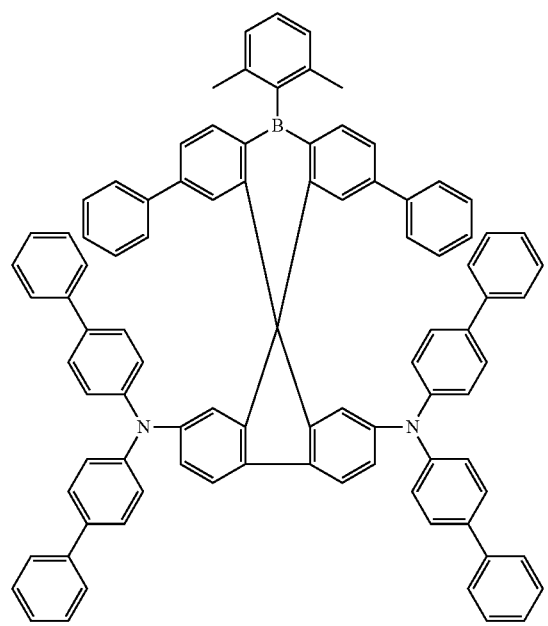
39
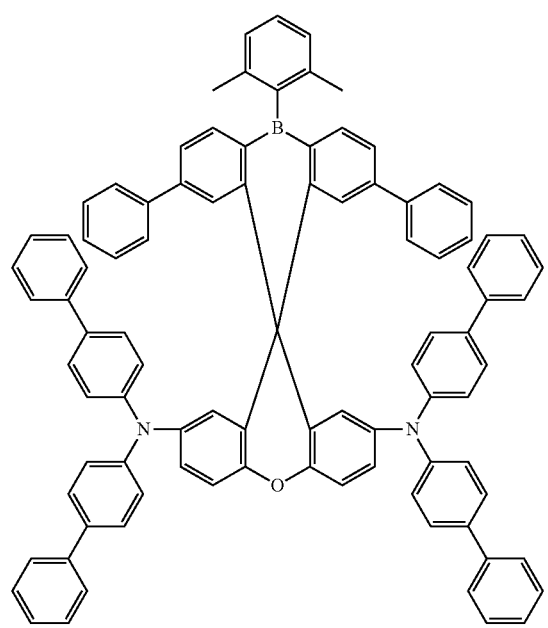

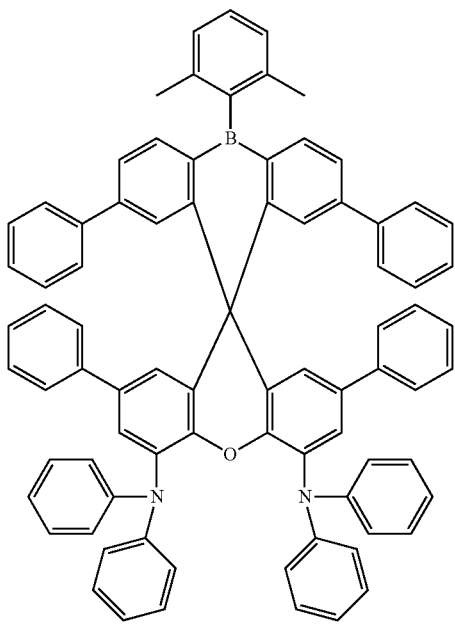

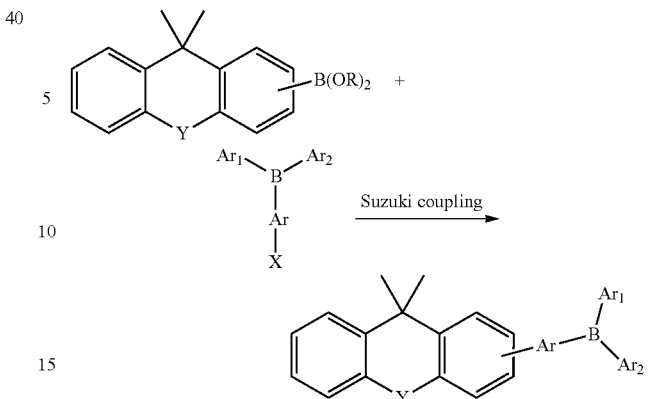

Provided that the conditions specified in claim 1 are complied with, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing compounds comprising structures of formula (I) and/or (II) by reacting at least one aryllithium compound with at least one haloborane and/or at least one borinic ester.

A preparation of compounds comprising structures of formula (I) is shown by way of example in the following scheme:

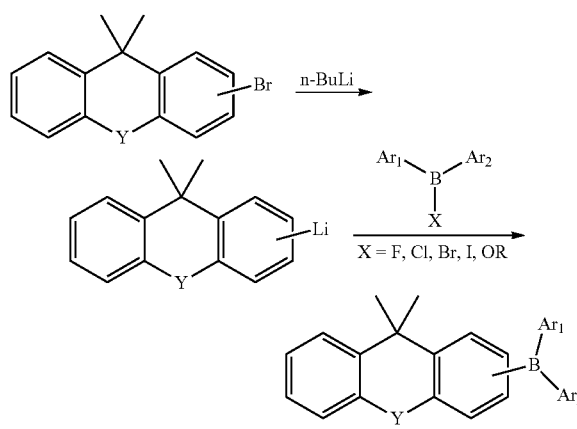

The present invention further provides a process for preparing compounds comprising structures of the formula (I) and/or (II) via coupling reactions.

This method is illustrated by way of example via Suzuki coupling from aryl bromides and arylboronic acids:

R═OH, O-Alkyl

Particularly suitable and preferred coupling reactions which all lead to C—C bonds are those according to BUCHWALD, SUZUKI, YAMAMOTO, STILLE, HECK, NEGISHI, SONOGASHIRA and HIYAMA.

The principles of the preparation processes detailed above are known in principle from the literature for similar compounds and can be adapted easily by the person skilled in the art to the preparation of the compounds of the invention.

It is possible by these processes, if necessary followed by purification, for example recrystallization or sublimation, to obtain the compounds of the invention comprising structures of the formula (I) and/or formula (II) in high purity, preferably more than 99% (determined by means of $^1$H NMR and/or HPLC).

The compounds of the invention may also have suitable substituents, for example by relatively long alkyl groups (about 4 to 20 carbon atoms), especially branched alkyl groups, or optionally substituted aryl groups, for example xylyl, mesityl or branched terphenyl or quaterphenyl groups, which bring about solubility in standard organic solvents, for example toluene or xylene, at room temperature in a sufficient concentration soluble, in order to be able to process the complexes from solution. These soluble compounds are of particularly good suitability for processing from solution, for example by printing methods. In addition, it should be emphasized that the compounds of the invention comprising at least one structure of the formulae (I) and/or (II) already have enhanced solubility in these solvents.

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds of the invention and polymers may be used in the form of a crosslinked or uncrosslinked layer.

The invention therefore further provides oligomers, polymers or dendrimers containing one or more of the above-detailed structures of the formulae (I) and/or (II) or compounds of the invention, wherein one or more bonds in the compounds of the invention or in the structures of the formulae (I) and/or (II) to the polymer, oligomer or dendrimer are present. According to the linkage of the structures of the formulae (I) and/or (II) or of the compounds, these therefore form a side chain of the oligomer or polymer or are bonded within the main chain. The polymers, oligomers or dendrimers may be conjugated, partly conjugated or non-conjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers.

Preference is given to copolymers wherein the units of formulae (I) and/or (II) or the above-recited preferred embodiments are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

In addition, the present compounds may have a relatively low molecular weight. The present invention accordingly further provides a compound having a molecular weight of preferably not more than 10 000 g/mol, more preferably not more than 5000 g/mol and especially preferably not more than 3000 g/mol.

In addition, it is a feature of preferred compounds that they are sublimable. These compounds generally have a molar mass of less than about 1200 g/mol.

Additionally of particular interest are compounds of the invention which feature a high glass transition temperature. In this connection, preference is given especially to compounds of the invention comprising structures of the general formulae (I) and (II) having a glass transition temperature of at least 70° C., more preferably of at least 110° C., even more preferably of at least 125° C. and especially preferably of at least 150° C., determined in accordance with DIN 51005.

The present invention still further provides a formulation comprising a compound of the invention or an oligomer, polymer or dendrimer of the invention and at least one further compound. The further compound may preferably be a solvent. The further compound may alternatively be a further organic or inorganic compound which is likewise used in the electronic device, for example a matrix material. This further compound may also be polymeric.

Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylinaphthalene, pentylbenzene, hexylbenzene, heptylbenzene, octylbenzene, 1,1-bis(3,4-dimethylphenyl)ethane or mixtures of these solvents.

The present invention still further provides a composition comprising a compound of the invention and at least one further organic functional material selected from the group consisting of fluorescent emitters, phosphorescent emitters, host materials, matrix materials, electron transport materials, electron injection materials, hole conductor materials, hole injection materials, electron blocker materials and hole blocker materials.

The present invention therefore also relates to a composition comprising at least one compound comprising structures of formula (I) and/or formula (II) and at least one further matrix material. According to a particular aspect of the present invention, the further matrix material has hole-transporting properties.

The present invention further provides a composition comprising at least one compound comprising at least one structure of formula (I) and/or (II) and at least one wide band gap material, a wide band gap material being understood to mean a material in the sense of the disclosure of U.S. Pat. No. 7,294,849. These systems exhibit particularly advantageous performance data in electroluminescent devices.

Preferably, the additional compound may have a band gap of 2.5 eV or more, preferably 3.0 eV or more, very preferably of 3.5 eV or more. One way of calculating the band gap is via the energy levels of the highest occupied molecular orbital (HOMO) and the lowest unoccupied molecular orbital (LUMO), as detailed by way of example above.

The present invention also relates to a composition comprising at least one compound comprising structures of formula (I) and/or formula (II) and at least one phosphorescent emitter, the term "phosphorescent emitter" also being understood to mean phosphorescent dopants.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent dopants are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent dopants, compounds containing copper, molybdenum, tungsten, rhenium, ruthenium, osmium, rhodium, iridium, palladium, platinum, silver, gold or europium, especially compounds containing iridium, platinum or copper.

In the context of the present application, all luminescent iridium, platinum or copper complexes are considered to be phosphorescent compounds.

Examples of phosphorescent dopants are adduced in a section which follows.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

Preferred phosphorescent dopants for use in mixed matrix systems are the preferred phosphorescent dopants specified hereinafter.

Examples of phosphorescent dopants can be found in applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used for phosphorescent OLEDs according to the prior art and as known to those skilled in the art in the field of organic electroluminescent devices are suitable for use in the inventive devices.

Explicit examples of phosphorescent dopants are adduced in the following table:

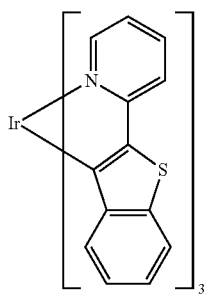

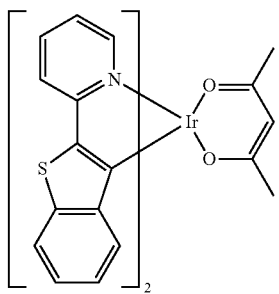

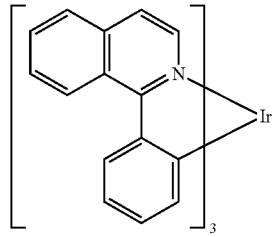

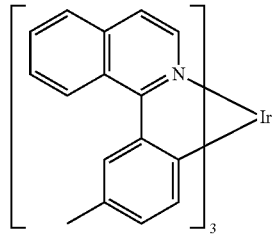

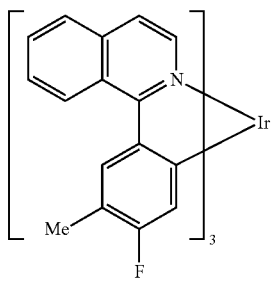

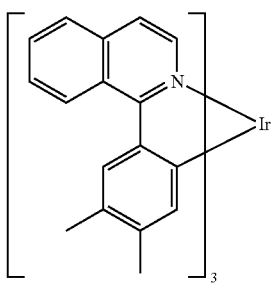

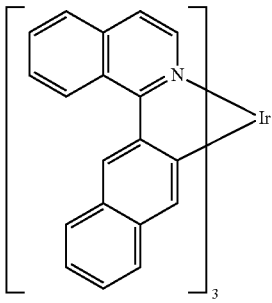

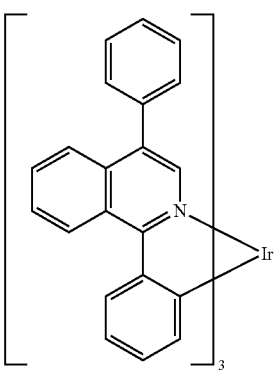

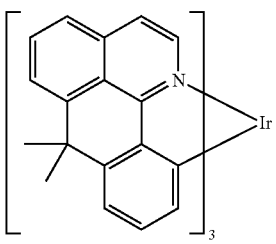

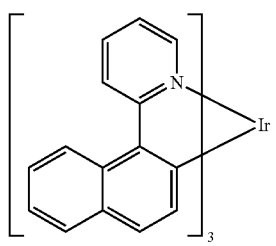
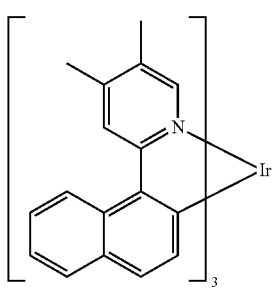
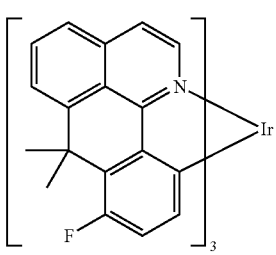
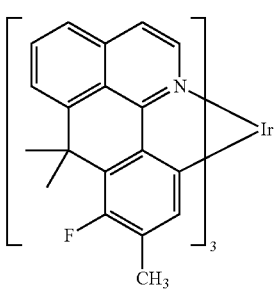
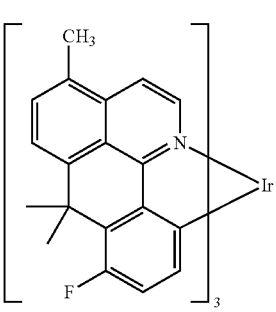
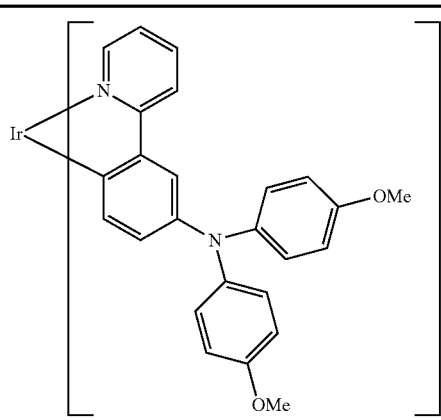
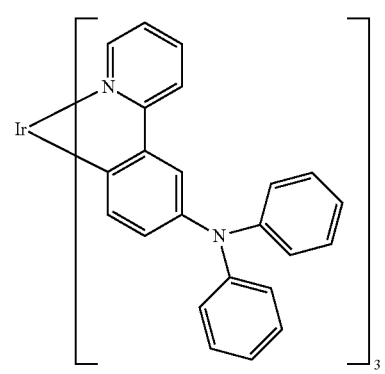
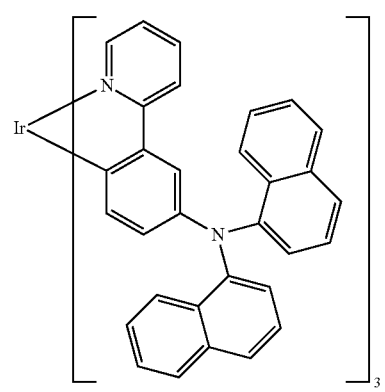
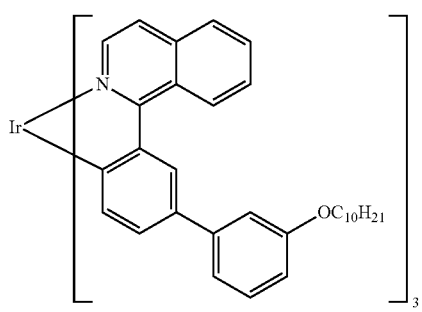

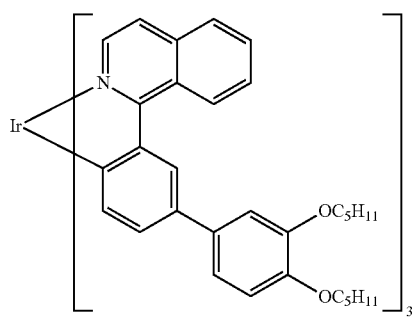
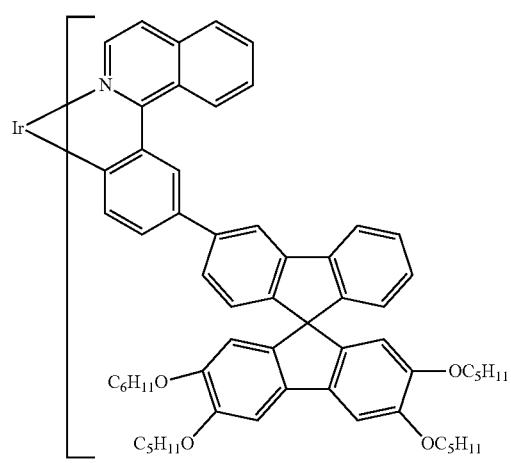
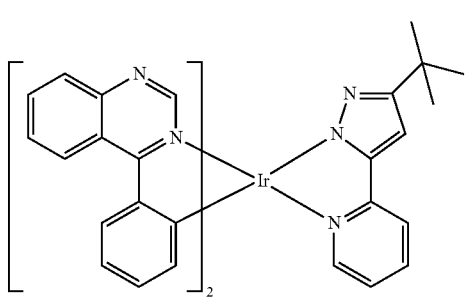
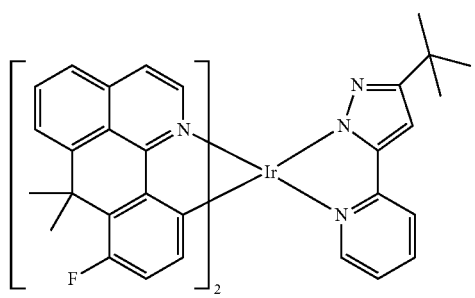
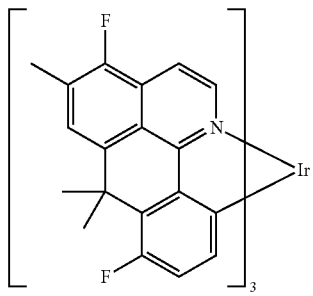
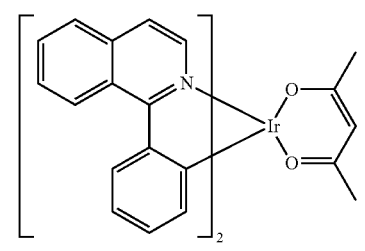
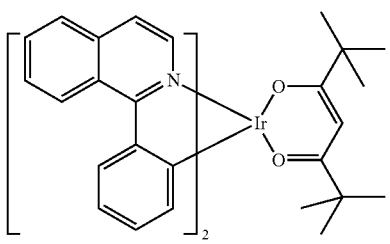
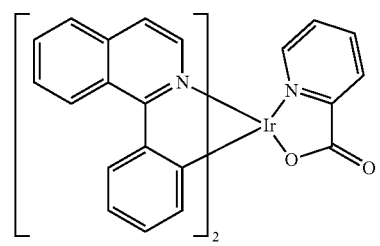
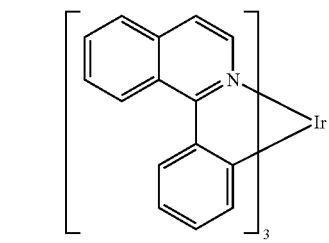
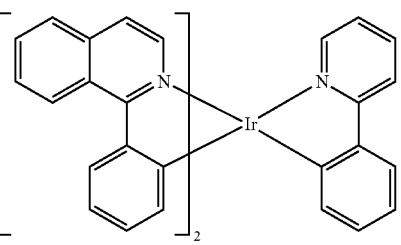

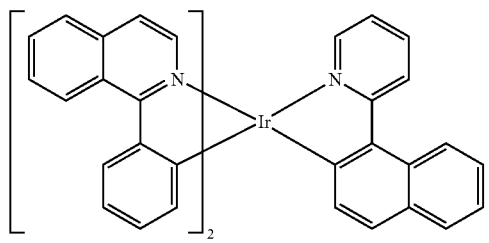
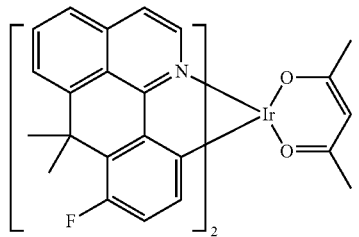
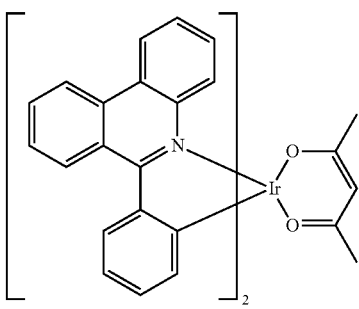
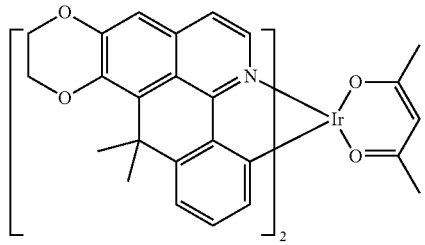
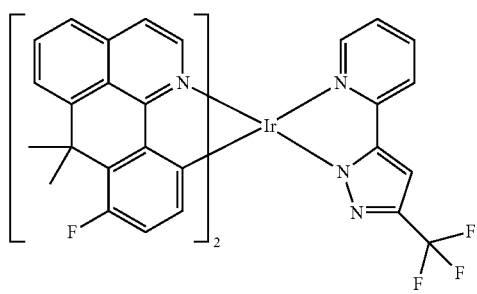
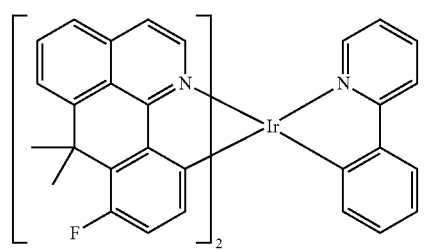
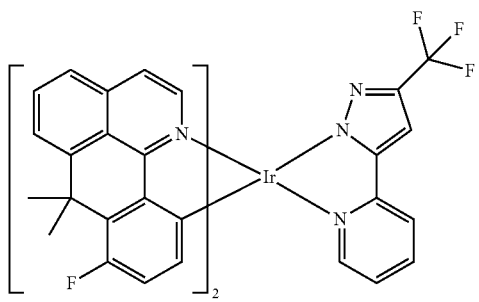
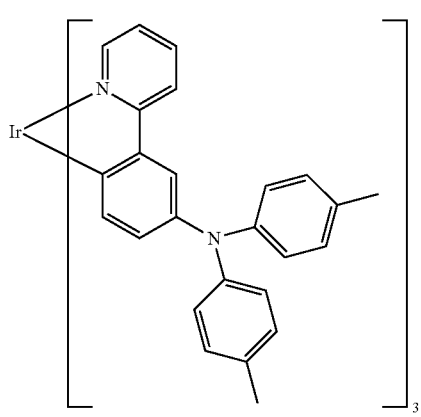
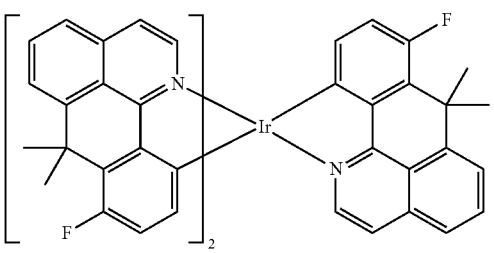
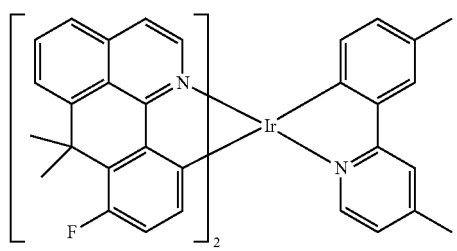
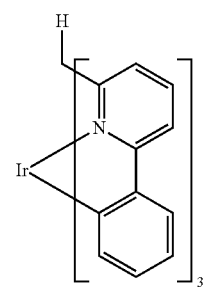

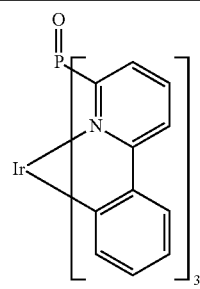
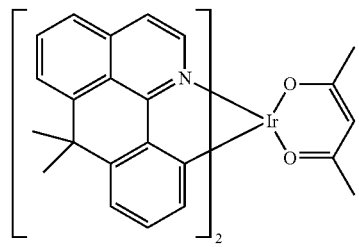
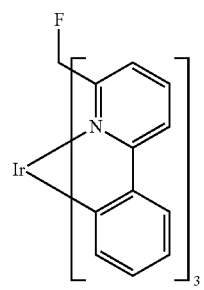
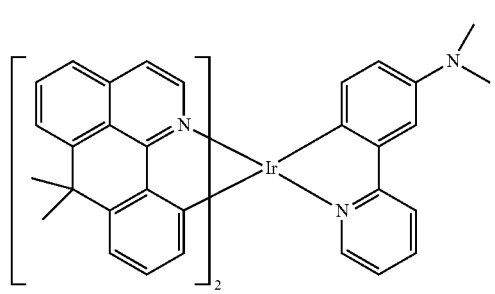
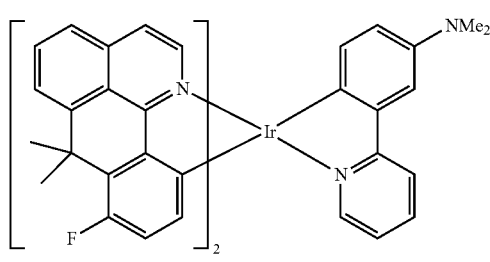
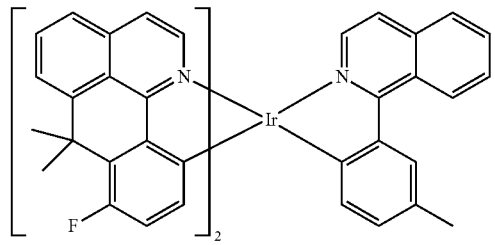
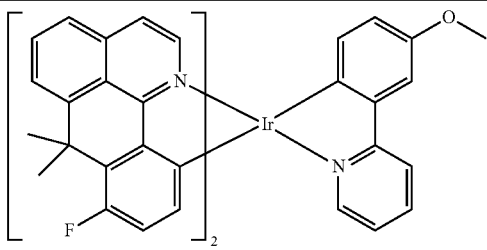
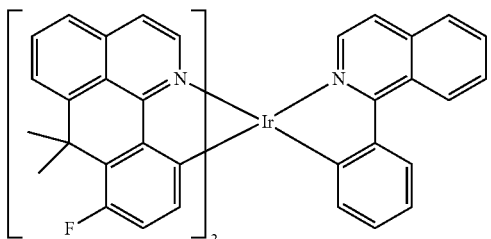
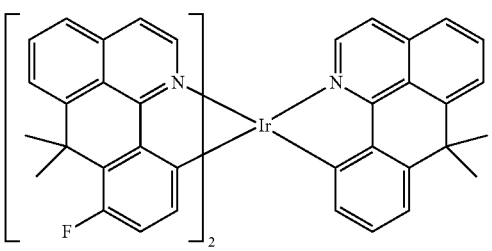
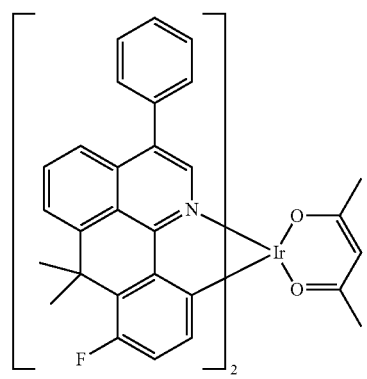
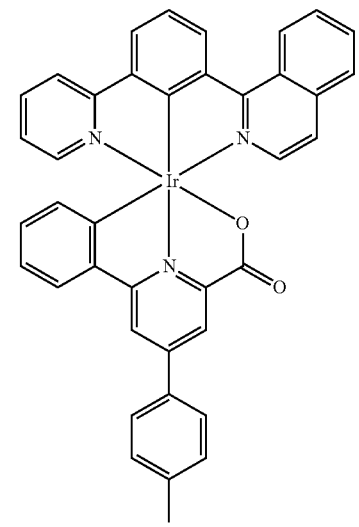

-continued
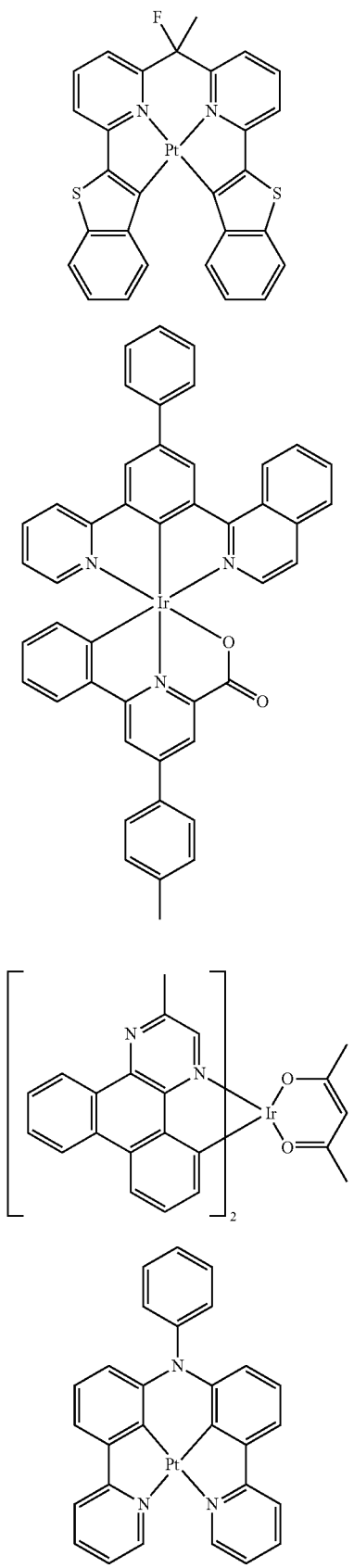
-continued
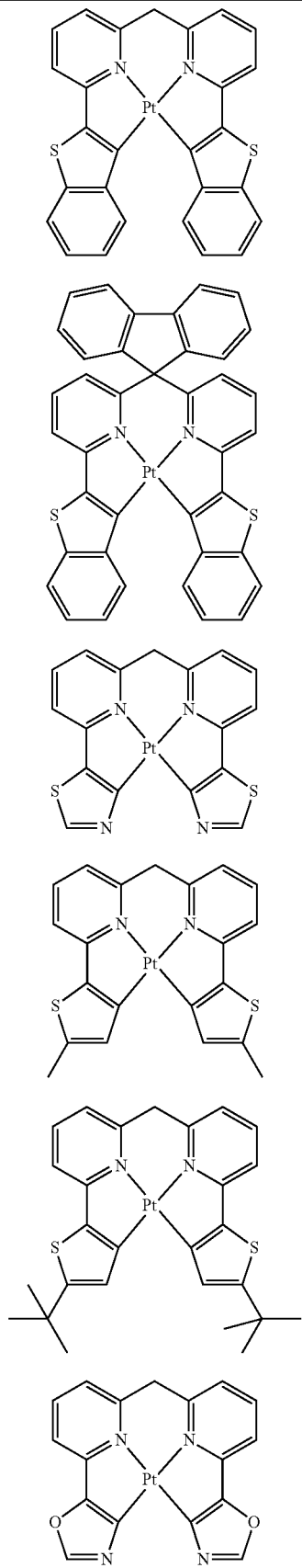

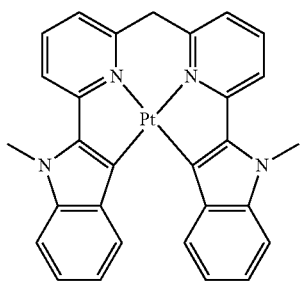
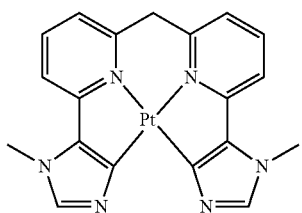
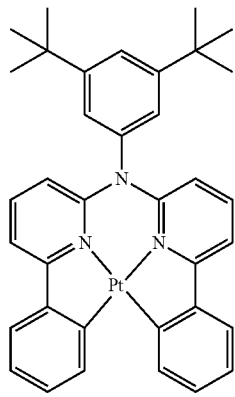
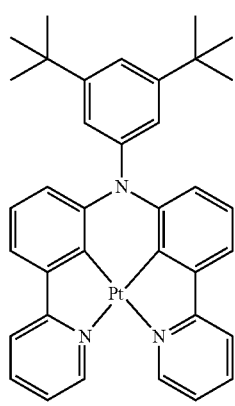
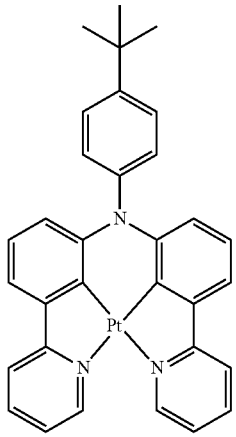
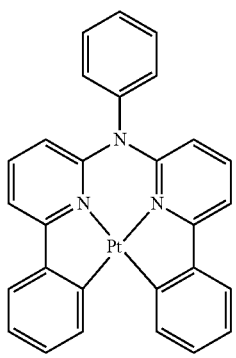
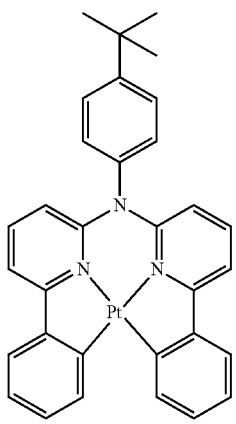
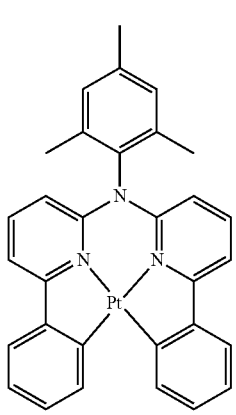

| 45 -continued | 46 -continued |
|---|---|
| 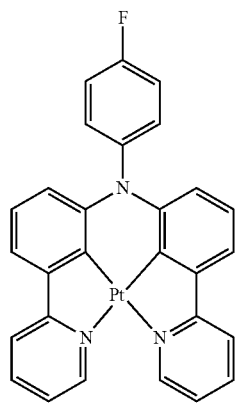 | 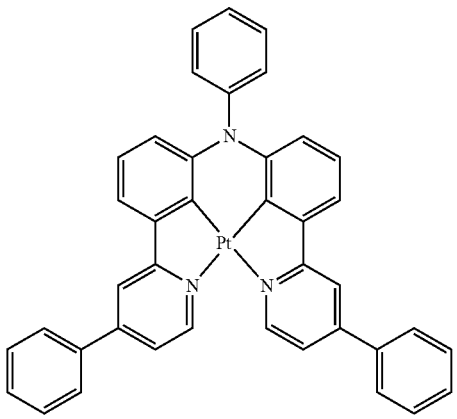 |
| 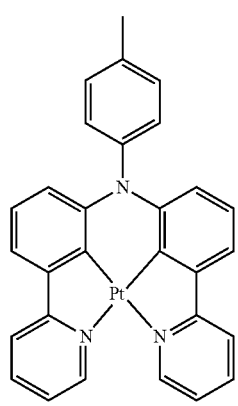 | 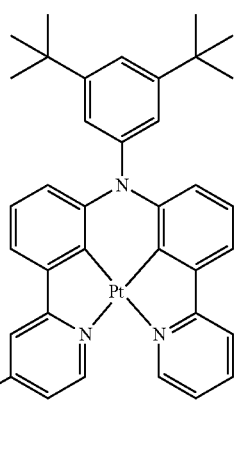 |
| 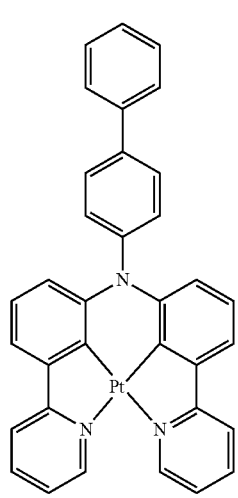 | 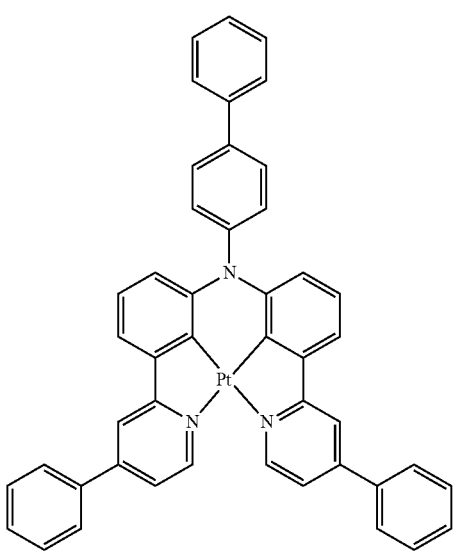 |

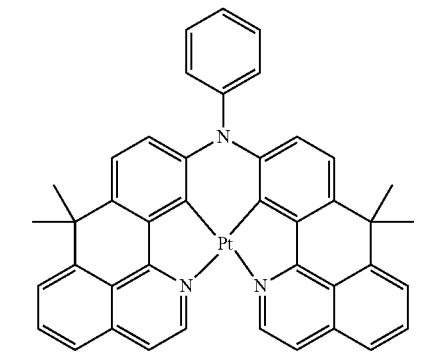
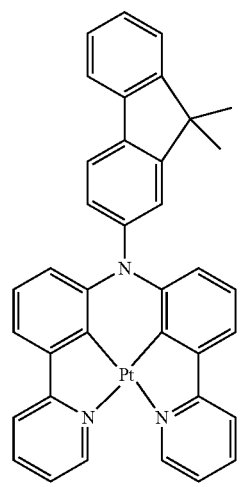
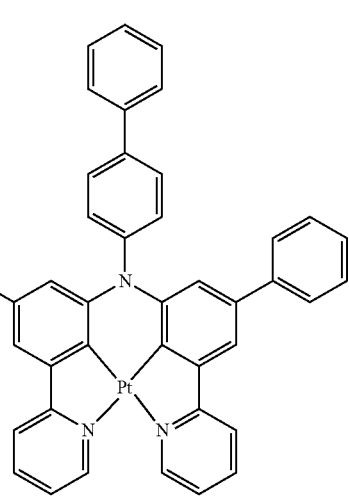
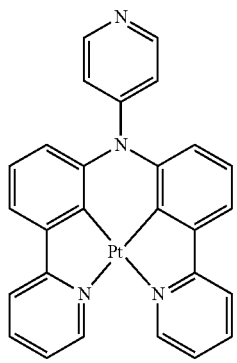
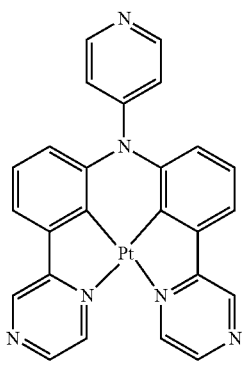
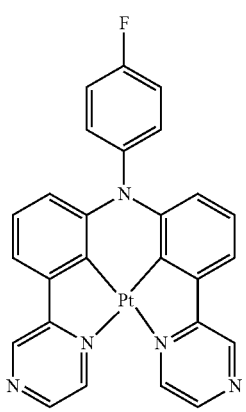
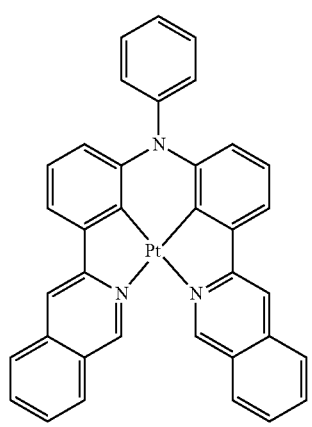

-continued
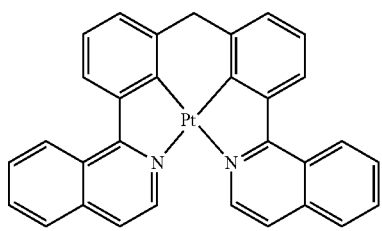
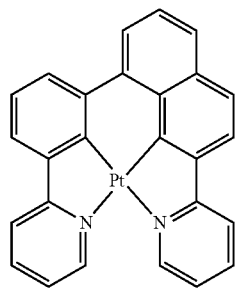
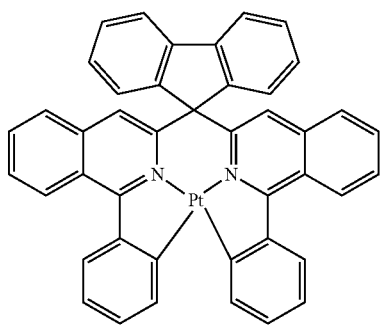
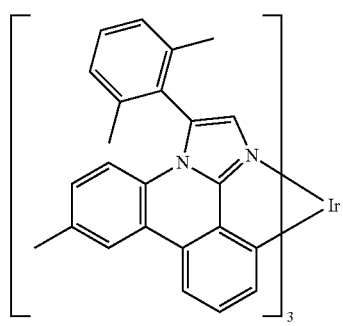
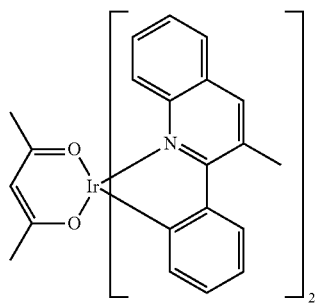
-continued
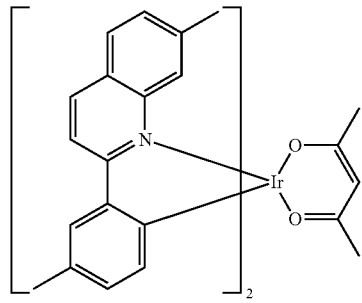
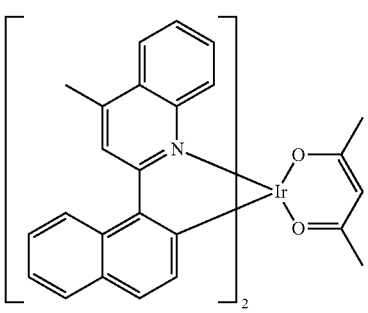
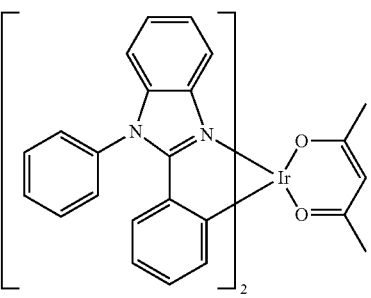
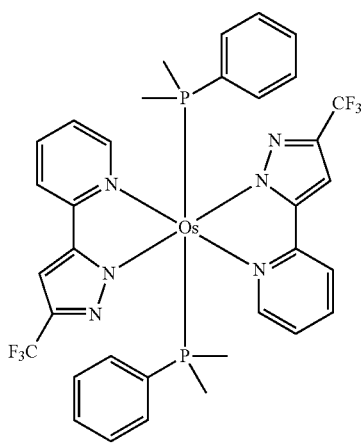
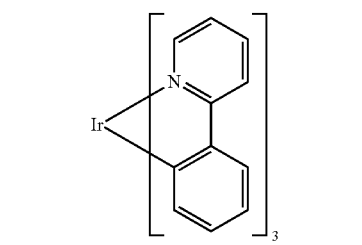

51
-continued
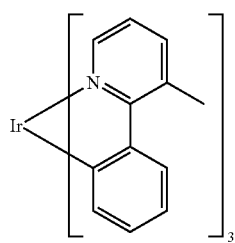
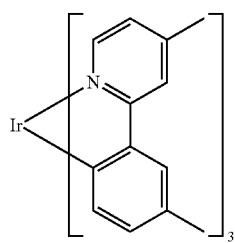
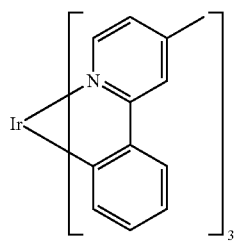
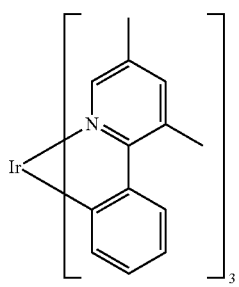
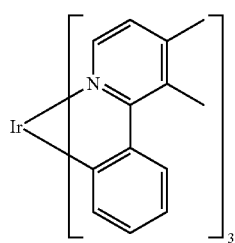
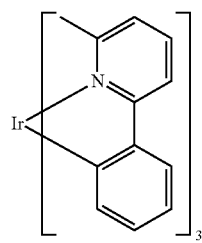
52
-continued
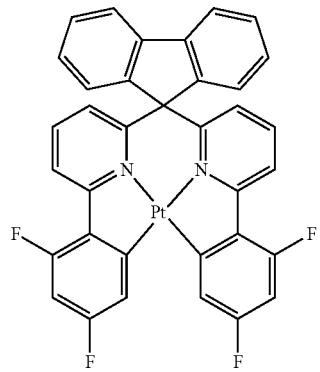
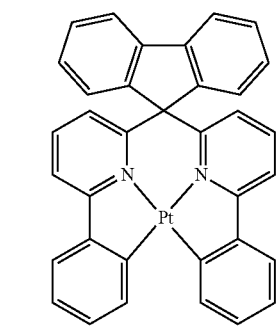
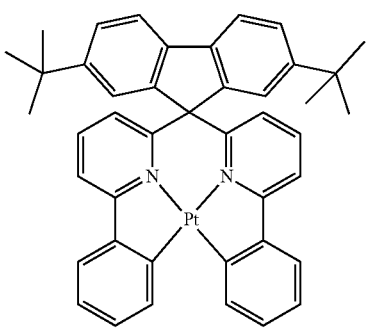
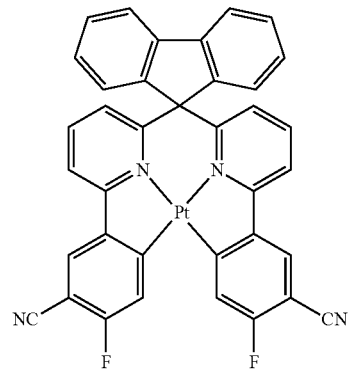

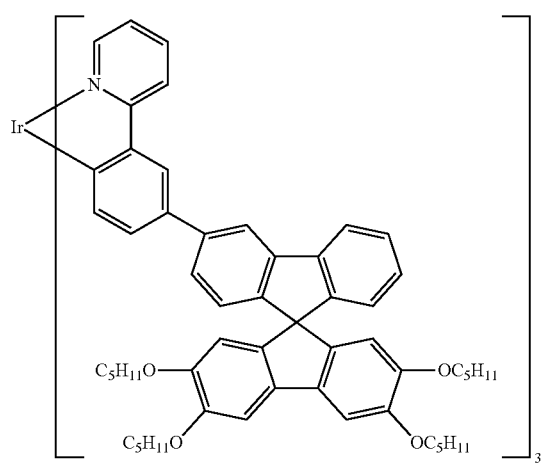
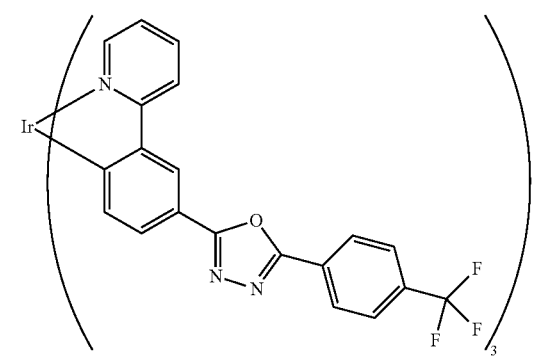
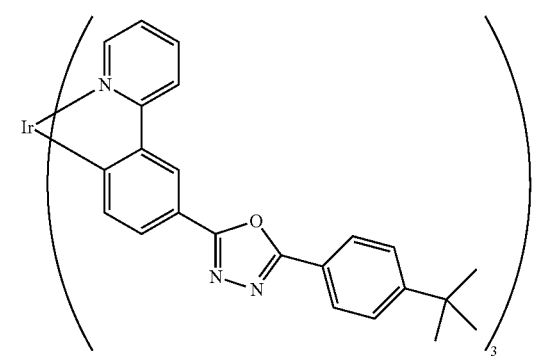
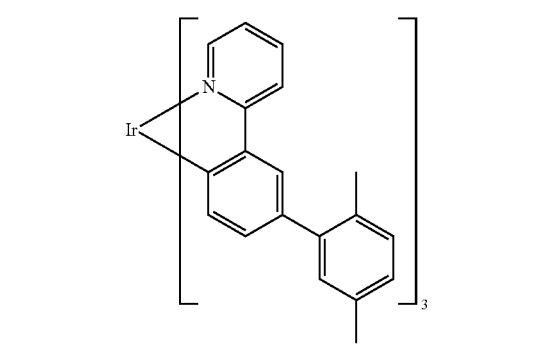
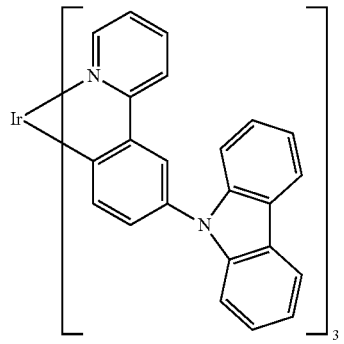
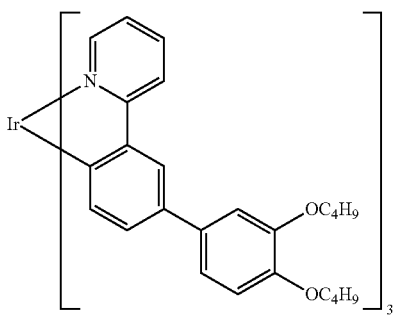
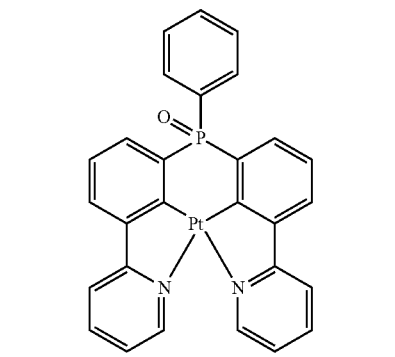
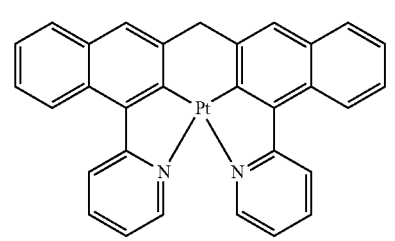
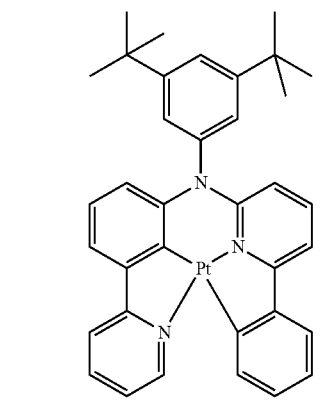

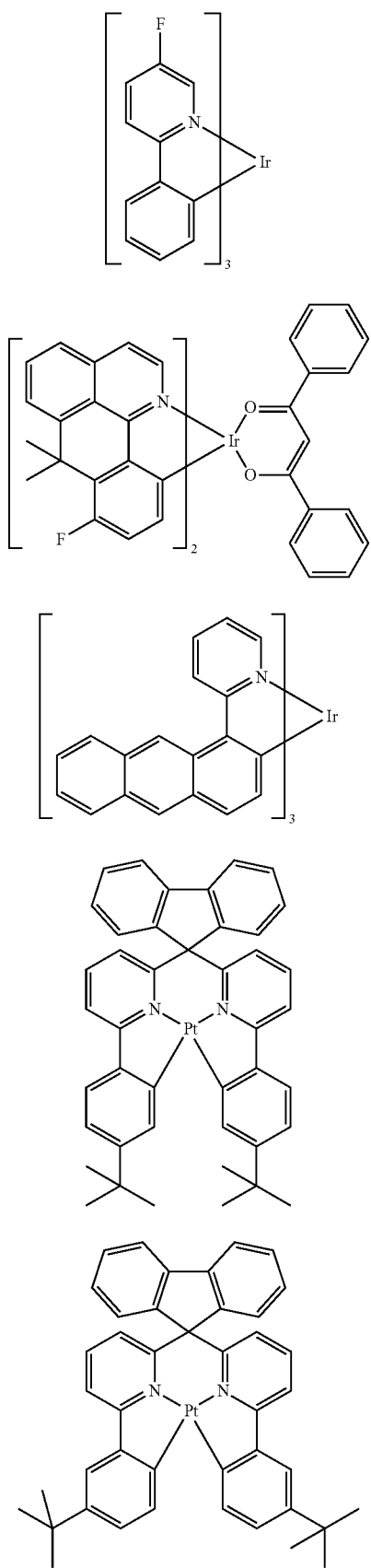
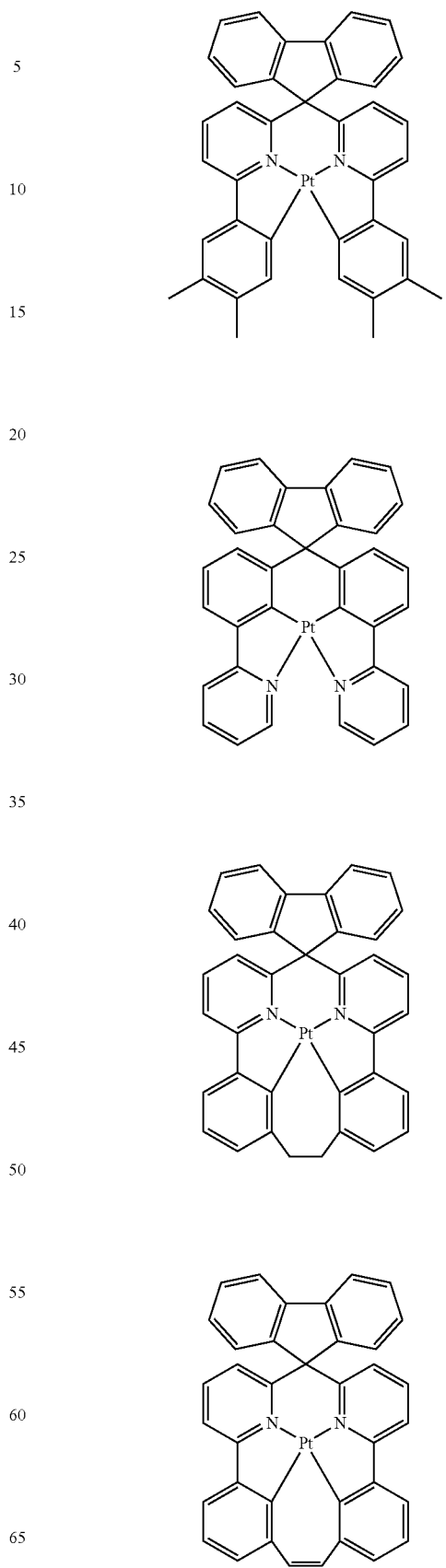

57
-continued
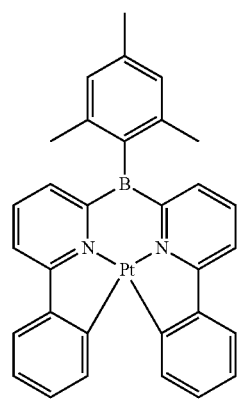
58
-continued
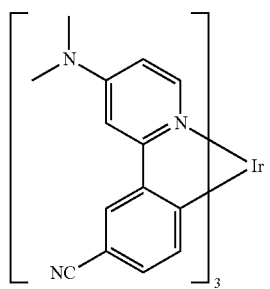
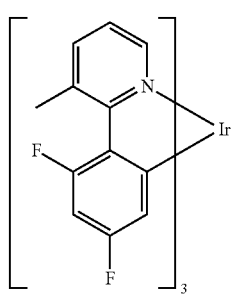
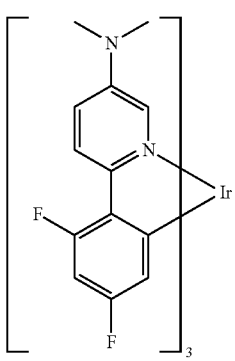
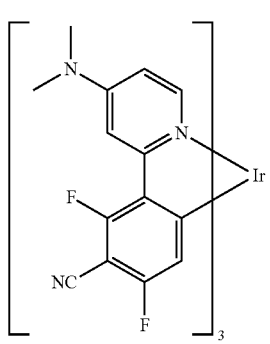
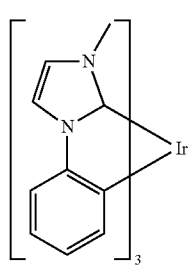

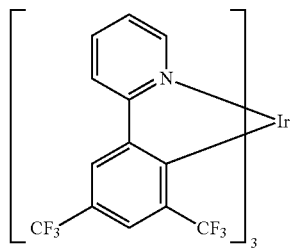
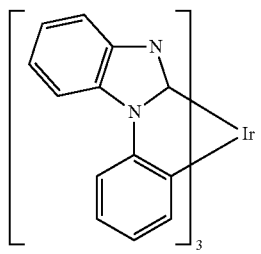
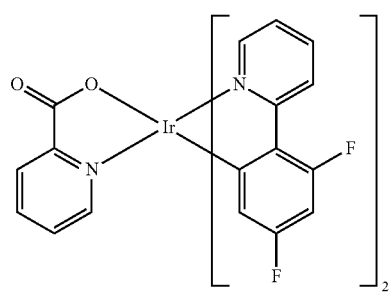
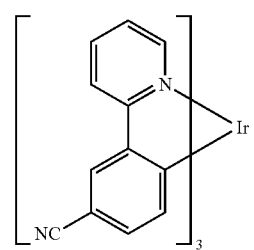
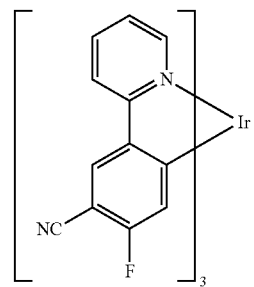
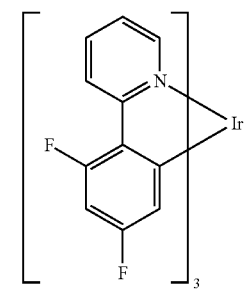
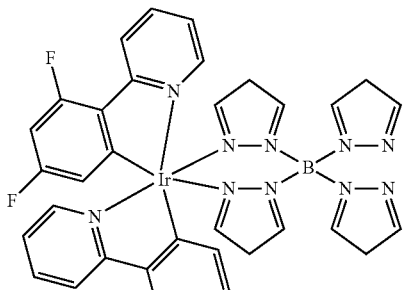
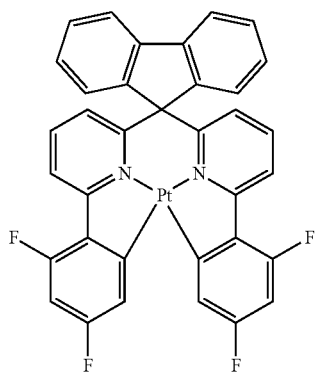
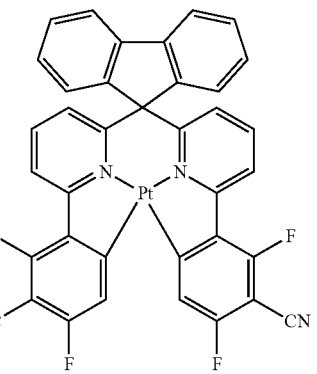
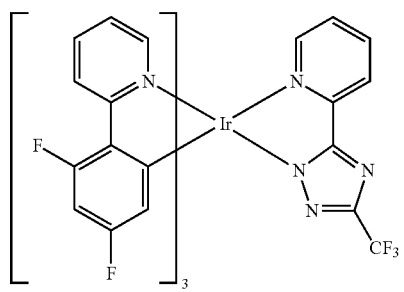

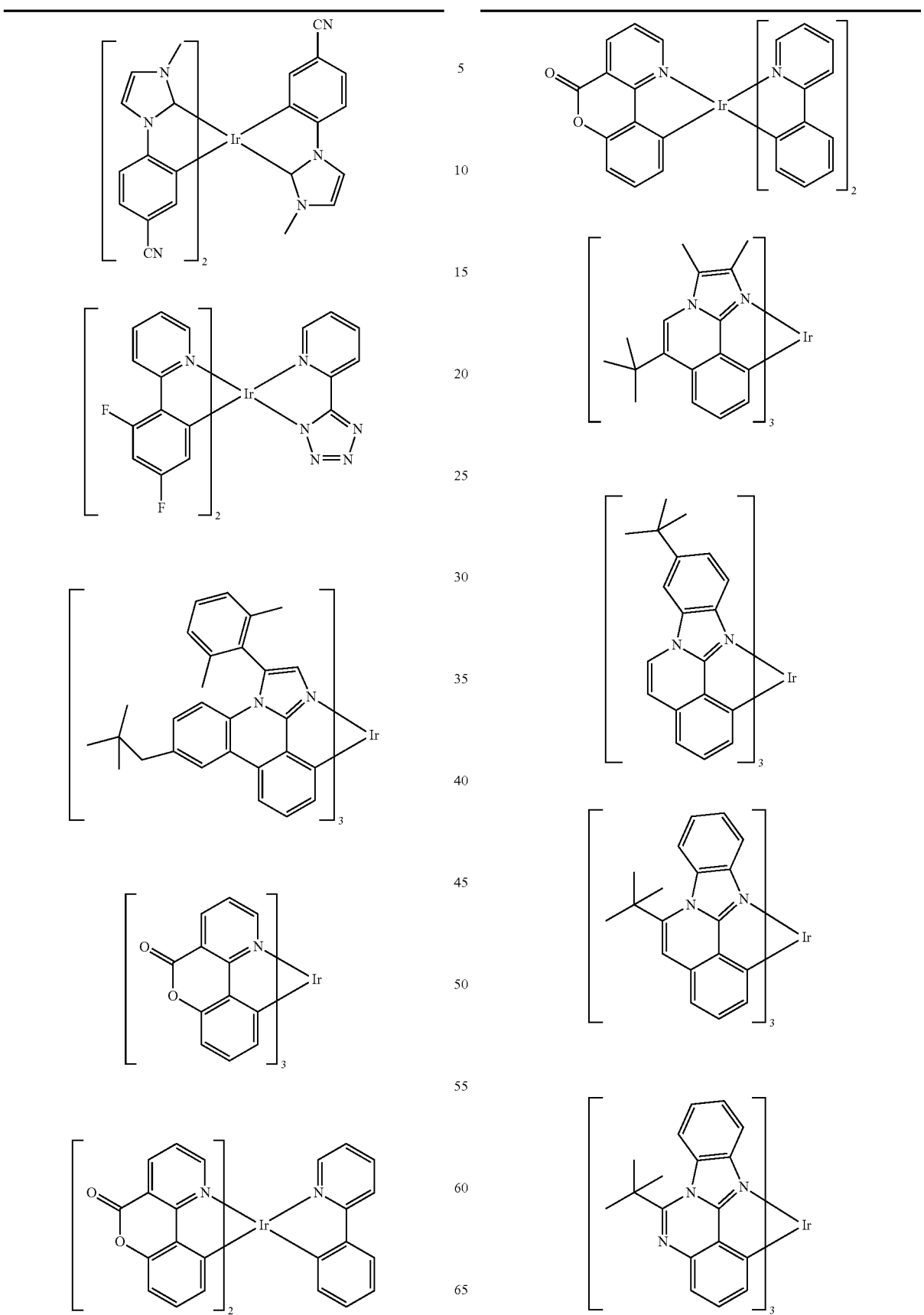

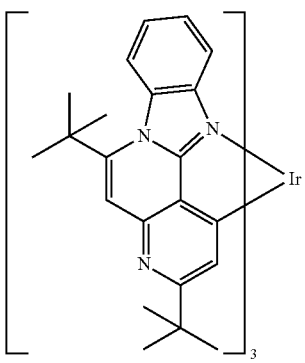
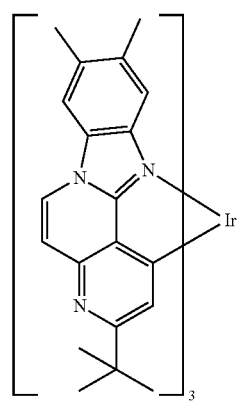
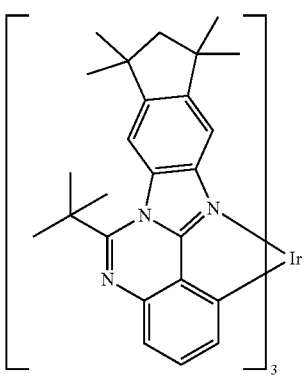
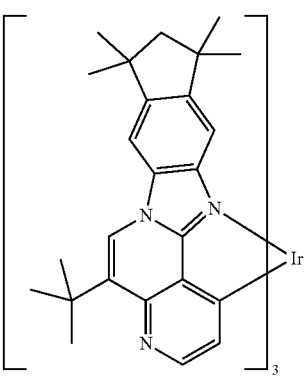
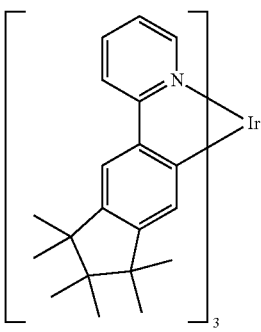
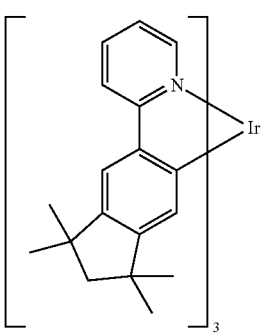
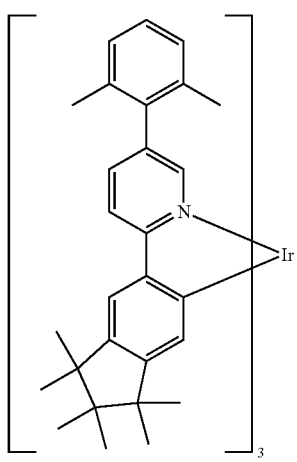
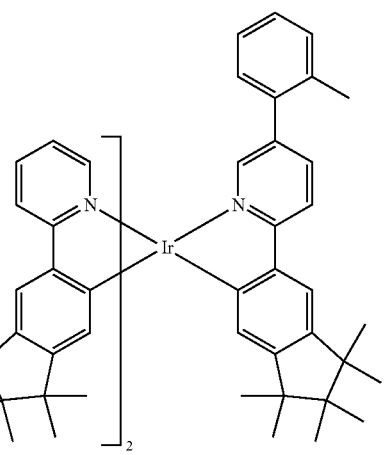

-continued
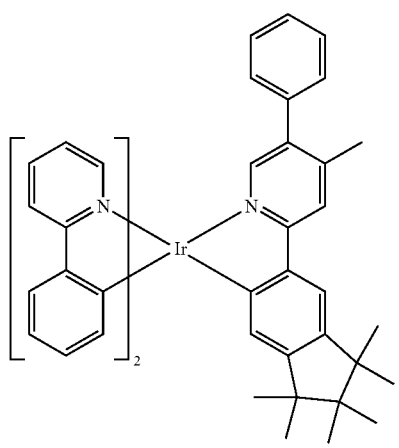
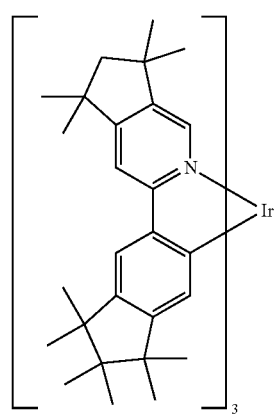
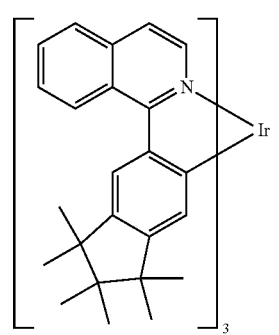
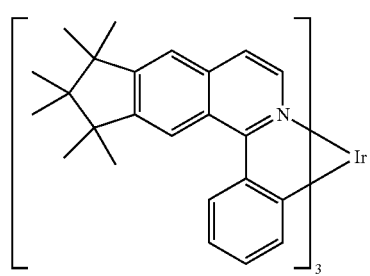
-continued
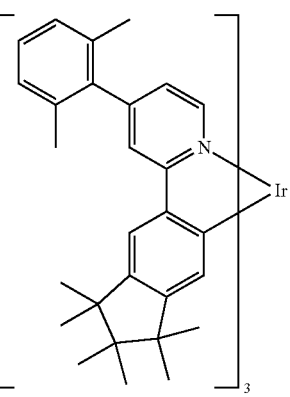
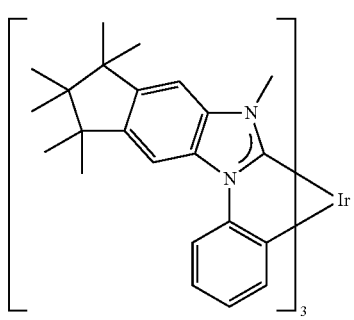
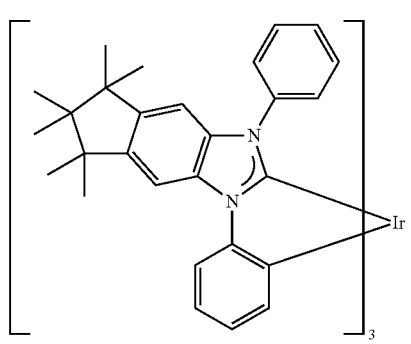
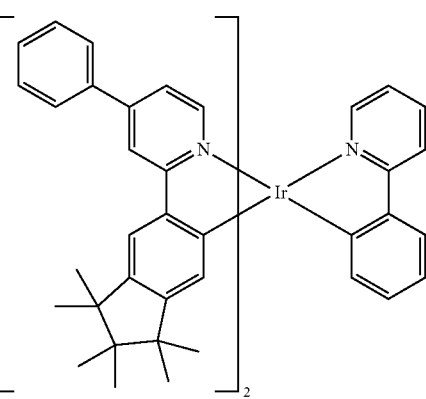

-continued

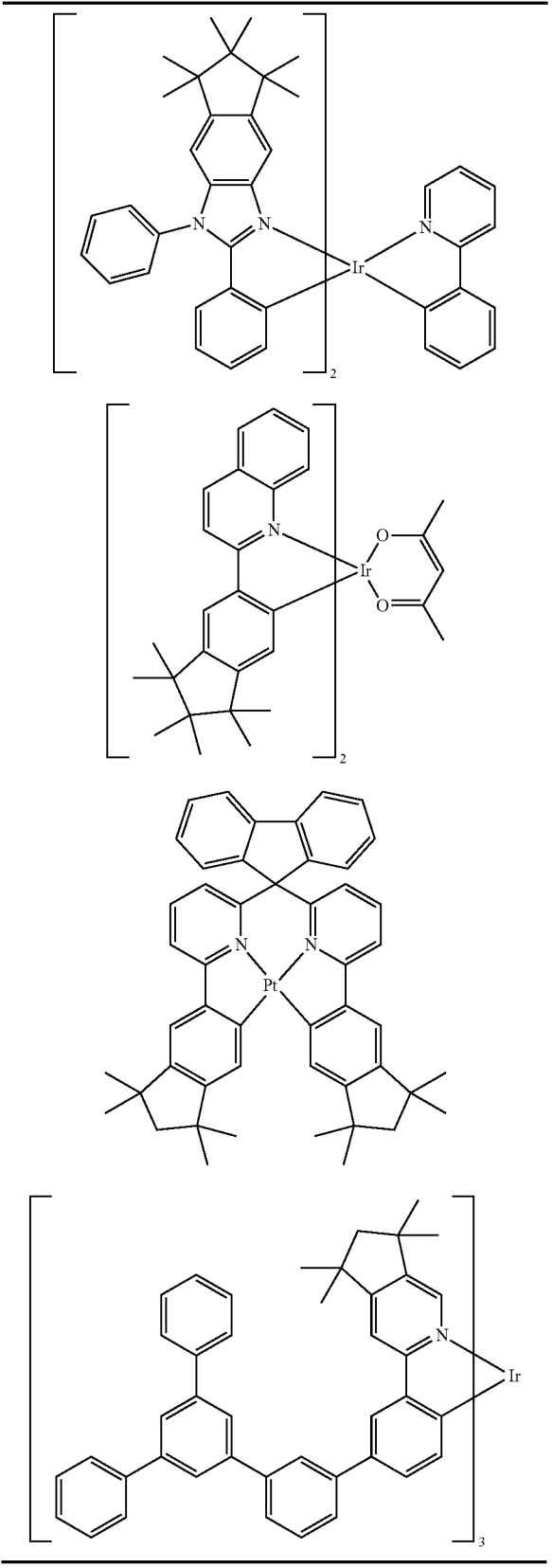

The above-described compound comprising structures of the formulae (I) and/or (II) or the above-detailed preferred embodiments can preferably be used as active component in an electronic device. An electronic device is understood to mean any device comprising anode, cathode and at least one layer, said layer comprising at least one organic or organo-metallic compound. The electronic device of the invention thus comprises anode, cathode and at least one layer containing at least one compound comprising structures of the formulae (I) and/or (II). Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) and organic laser diodes (O-lasers), containing at least one compound comprising structures of the formulae (I) and/or (II) in at least one layer. Particular preference is given to organic electroluminescent devices. Active components are generally the organic or inorganic materials introduced between the anode and cathode, for example charge injection, charge transport or charge blocker materials, but especially emission materials and matrix materials. The compounds of the invention exhibit particularly good properties as emission material in organic electroluminescent devices. A preferred embodiment of the invention is therefore organic electroluminescent devices. In addition, the compounds of the invention can be used for production of singlet oxygen or in photocatalysis.

The organic electroluminescent device comprises cathode, anode and at least one emitting layer. Apart from these layers, it may comprise further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as $MoO_3$ or $WO_3$ or with (per)fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. The system may also be a hybrid system wherein one or more layers fluoresce and one or more other layers phosphoresce.

In a preferred embodiment of the invention, the organic electroluminescent device contains the compound of the invention comprising structures of formula (I) and/or (II) or the above-detailed preferred embodiments as matrix material, preferably as electron-conducting matrix material, in one or more emitting layers, preferably in combination with a further matrix material, preferably a hole-conducting matrix material. An emitting layer comprises at least one emitting compound.

The matrix material used may generally be any materials which are known for the purpose according to the prior art. The triplet level of the matrix material is preferably higher than the triplet level of the emitter.

Suitable matrix materials for the compounds of the invention are ketones, phosphine oxides, sulfoxides and sulfones, for example according to WO 2004/013080, WO 2004/093207, WO 2006/005627 or WO 2010/006680, triarylamines, carbazole derivatives, e.g. CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example according to WO 2007/063754 or WO 2008/056746, indenocarbazole derivatives, for example according to WO 2010/136109 or WO 2011/000455, azacarbazoles, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, diazasilole derivatives, for example according to WO 2010/054729, diazaphosphole derivatives, for example according to WO 2010/054730, triazine derivatives, for example according to WO 2010/015306, WO 2007/063754 or WO 2008/056746, zinc complexes, for example according to EP 652273 or WO 2009/062578, dibenzofuran derivatives, for example according to WO 2009/148015, or bridged carbazole derivatives, for example according to US 2009/0136779, WO 2010/050778, WO 2011/042107 or WO 2011/088877.

It may also be preferable to use a plurality of different matrix materials as a mixture, especially at least one electron-conducting matrix material and at least one hole-conducting matrix material. Preference is likewise given to the use of a mixture of a charge-transporting matrix material and an electrically inert matrix material having no significant involvement, if any, in the charge transport, as described, for example, in WO 2010/108579.

It is further preferable to use a mixture of two or more triplet emitters together with a matrix. In this case, the triplet emitter having the shorter-wave emission spectrum serves as co-matrix for the triplet emitter having the longer-wave emission spectrum.

More preferably, a compound of the invention comprising structures of formula (I) and/or formula (II), in a preferred embodiment, can used as matrix material in an emission layer of an organic electronic device, especially in an organic electroluminescent device, for example in an OLED or OLEC. In this case, the matrix material containing compound comprising structures of formula (I) and/or formula (II) is present in the electronic device in combination with one or more dopants, preferably phosphorescent dopants.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the dopant is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a further preferred embodiment of the invention, the compound comprising structures of formula (I) and/or formula (II) is used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The desired electron-transporting and hole-transporting properties of the mixed matrix components may, however, also be combined mainly or entirely in a single mixed matrix component, in which case the further mixed matrix component(s) fulfill(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

Particularly suitable matrix materials which can be used in combination with the inventive compounds as matrix components of a mixed matrix system are selected from the preferred matrix materials specified below for phosphorescent dopants or the preferred matrix materials for fluorescent dopants, according to what type of dopant is used in the mixed matrix system.

The present invention further provides an electronic device, preferably an organic electroluminescent device, comprising one or more compounds of the invention and/or at least one oligomer, polymer or dendrimer of the invention in one or more electron-conducting layers, as electron-conducting compound.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/ NiOx, Al/PtOx) may also be preferred. For some applications, at least one of the electrodes has to be transparent or partly transparent in order to enable either the irradiation of the organic material (O-SC) or the emission of light (OLED/ PLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled. Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices is severely shortened in the presence of water and/or air.

Additionally preferred is an electronic device, especially an organic electroluminescent device, which is characterized in that one or more layers are coated by a sublimation process. In this case, the materials are applied by vapor deposition in vacuum sublimation systems at an initial pressure of typically less than $10^{-5}$ mbar, preferably less than $10^{-6}$ mbar. It is also possible that the initial pressure is even lower or even higher, for example less than $10^{-7}$ mbar.

Preference is likewise given to an electronic device, especially an organic electroluminescent device, which is characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example, M. S. Arnold et al., Appl. Phys. Lett. 2008, 92, 053301).

Preference is additionally given to an electronic device, especially an organic electroluminescent device, which is characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The electronic device, especially the organic electroluminescent device can also be produced as a hybrid system by applying one or more layers from solution and applying one or more other layers by vapor deposition. For example, it is possible to apply an emitting layer comprising a compound of the invention comprising structures of formula (I) and/or (II) and a matrix material from solution, and to apply a hole blocker layer and/or an electron transport layer thereto by vapor deposition under reduced pressure.

These methods are known in general terms to those skilled in the art and can be applied without difficulty to electronic devices, especially organic electroluminescent devices comprising compounds of the invention comprising structures of formula (I) and/or (II) or the above-detailed preferred embodiments.

The electronic devices of the invention, especially organic electroluminescent devices, are notable for one or more of the following surprising advantages over the prior art:

1. Electronic devices, especially organic electroluminescent devices, comprising compounds, oligomers, polymers or dendrimers having structures of formula (I) and/or (II), especially as electron-conducting materials, have a very good lifetime.
2. Electronic devices, especially organic electroluminescent devices, comprising compounds, oligomers, polymers or dendrimers having structures of formula (I) and/or (II) as electron-conducting materials have excellent efficiency. More particularly, efficiency is much higher compared to analogous compounds containing no structural unit of formula (I) or formula (II).
3. The compounds, oligomers, polymers and dendrimers of the invention having structures of the formula (I) and/or (II) exhibit very high stability and lead to compounds having a very long lifetime.
4. With compounds, oligomers, polymers or dendrimers having structures of formula (I) and/or (II), it is possible to avoid the formation of optical loss channels in electronic devices, especially organic electroluminescent devices. As a result, these devices feature a high PL efficiency and hence high EL efficiency of emitters, and excellent energy transmission of the matrices to dopants.
5. The use of compounds, oligomers, polymers or dendrimers having structures of formula (I) and/or (II) in layers of electronic devices, especially organic electroluminescent devices, leads to a high mobility of the electron conductor structures.
6. Compounds, oligomers, polymers and dendrimers having structures of formula (I) and/or (II) feature excellent thermal stability, and compounds having a molar mass of less than about 1200 g/mol have good sublimability.
7. Compounds, oligomers, polymers and dendrimers having structures of formula (I) and/or (II) have excellent glass film formation.
8. Compounds, oligomers, polymers and dendrimers having structures of formula (I) and/or (II) form very good films from solutions.
9. The compounds, oligomers, polymers or dendrimers comprising structures of formula (I) and/or (I) have too surprisingly high triplet levels $T_1$.

These abovementioned advantages are not accompanied by a deterioration in the further electronic properties.

The present invention further provides for the use of a compound of the invention and/or an oligomer, polymer or dendrimer of the invention in an electronic device as hole blocker material, electron injection material and/or electron transport material.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, are themselves inventive and should not be regarded merely as some of the embodiments of the present invention. For these features, independent protection may be sought in addition to or as an alternative to any currently claimed invention.

The technical teaching disclosed with the present invention may be abstracted and combined with other examples.

The invention is illustrated in detail by the examples which follow, without any intention of restricting it thereby.

The person skilled in the art will be able to use the details given, without exercising inventive skill, to produce further electronic devices of the invention and hence to execute the invention over the entire scope claimed.

EXAMPLES

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective figures in square brackets or the numbers quoted for individual compounds relate to the CAS numbers of the compounds known from the literature.

General Preparation Method

A: Synthesis of the Synthons S

Example S1: 4-Bromospiro-9,9'-bifluorene

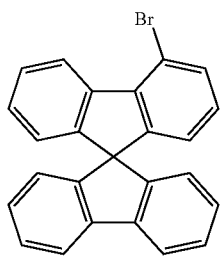 [SMILES: Brc1cccc2c1-c1ccccc1C21c2ccccc2-c2ccccc21]

To a solution, cooled to −78° C., of 250 g (785 mmol) of 2,2'-dibromobiphenyl in 2000 mL of THF are added dropwise, while stirring, 318 mL of n-BuLi, 2.5 M in n-hexane, and the mixture is stirred for a further 30 min. Then added dropwise is a solution of 144 g (785 mmol) of fluorene in 1000 mL of THF, the mixture is stirred for a further 30 min, the cooling bath is removed and the mixture is allowed to warm up to room temperature overnight. The solvent is substantially removed under reduced pressure, the residue is taken up in 2000 mL of glacial acetic acid, 200 mL of EtOH and 100 mL of conc. hydrochloric acid are added, and the mixture is heated under reflux for 2 h. After cooling, the precipitated solids are filtered off with suction and washed twice with 500 mL each time of glacial acetic acid and then three times with 300 mL each time of ethanol, and dried under reduced pressure. Yield: 265 g (667 mmol), 85%. Purity about 98% by NMR.

B: Synthesis of the Boranes

Variant 1

To a well-stirred solution or suspension, cooled to −78° C., of 100 mmol of a monobromide or 50 mmol of a dibromide or 33 mmol of a tribromide or 25 mmol of a tetrabromide in 1000 mL of THF are added dropwise 105 mmol of n-BuLi, 2.5 M in n-hexane, at such a rate that the temperature does not exceed −55° C. After the addition has ended, the mixture is stirred for a further 2 h, and then a solution of 110 mmol of fluoroborane in 200 mL of THF is added dropwise at such a rate that the temperature does not exceed −55° C. The mixture is stirred at −78° C. for 1 h and then allowed to warm up gradually to room temperature. After adding 50 mL of methanol, the solvent is substantially removed under reduced pressure, the residue is taken up in 500 mL of dichloromethane, and the organic phase is washed five times with 200 mL each time of water and once with 200 mL of saturated sodium chloride solution and then dried over magnesium sulfate. The residue obtained after removal of the solvent is purified by repeated recrystallization (for example from toluene, acetone, ethyl acetate in combination with alcohols such as methanol, ethanol, isopropanol, etc.) and final fractional sublimation twice under high vacuum (p about $10^{-6}$ to $10^{-6}$ mbar, T about 250-400° C.).

Example B1

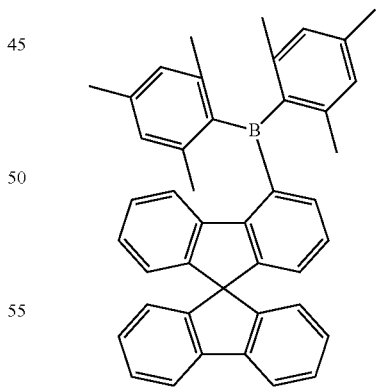

39.5 g (100 mmol) of 4-bromospiro-9,9'-bifluorene, S1, 42.0 mL (105) mmol of n-BuLi, 2.5 M in n-hexane, 29.5 g (110 mmol) of fluorodimesitylborane [436-59-9]. Recrystallization five times from toluene/EtOH. Fractional sublimation twice: p about $10^{-5}$ mbar, T=300-315° C. Yield: 19.2 g (34 mmol), 34%. Purity: 99.9% by HPLC.

In an analogous manner, it is possible to prepare the following compounds:

| Ex. | Reactant | Product | Yield |
|---|---|---|---|
| 1-Fluorene type ||||
| B2 | 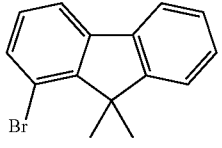<br>1225053/-54<br>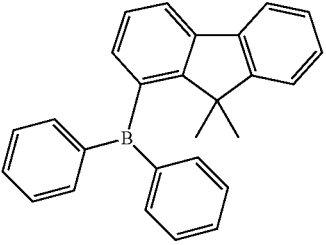 [SMILES: CC1(C)c2ccccc2-c2cccc(B(c3ccccc3)c3ccccc3)c21]<br>36140-35-9 | 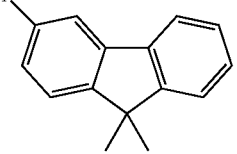 | 22% |
| 3-Fluorene type ||||
| B3 | 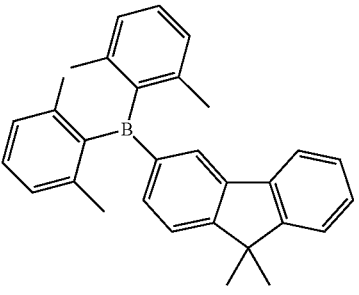 [SMILES: Cc1cccc(C)c1B(c1ccc2c(c1)-c1ccccc1C2(C)C)c1c(C)cccc1C]<br>1190360-23-6<br>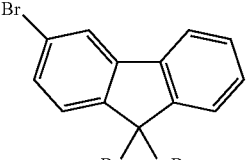<br>124855-14-7 | 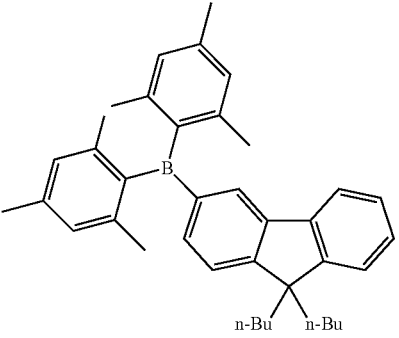 | 35% |
| B4 | <br>1246026-60-7<br><br>436-59-9 |  | 30% |

-continued
| Ex. | Reactant | Product | Yield |
|---|---|---|---|
| B5 | 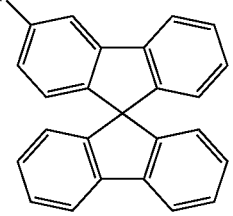 1361227-58-8 <br> 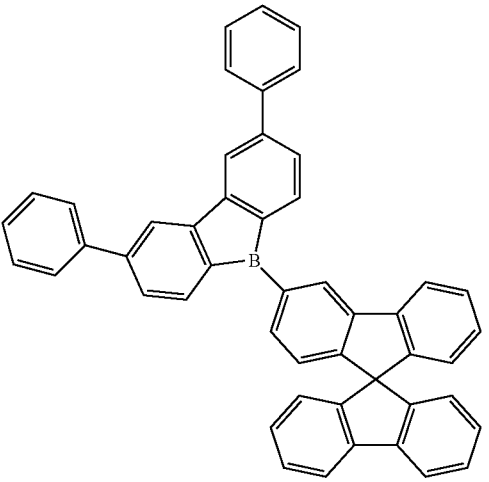 [SMILES: c1ccc(-c2ccc3c(c2)-c2cc(-c4ccccc4)ccc2B3c2ccc3c(c2)-c2ccccc2C32c3ccccc3-c3ccccc32)cc1] 1361252-26-7 | 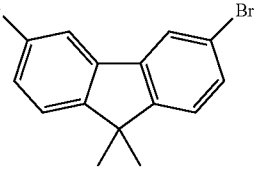 | 28% |
| B6 | 865702-19-8 <br> 123168-21-8 | | 18% |
| B7 | 1319162-41-8 <br> 436-59-9 | | 36% |

-continued
| Ex. | Reactant | Product | Yield |
|---|---|---|---|
| B8 | 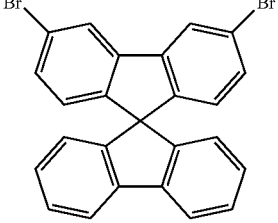 1373114-50-1 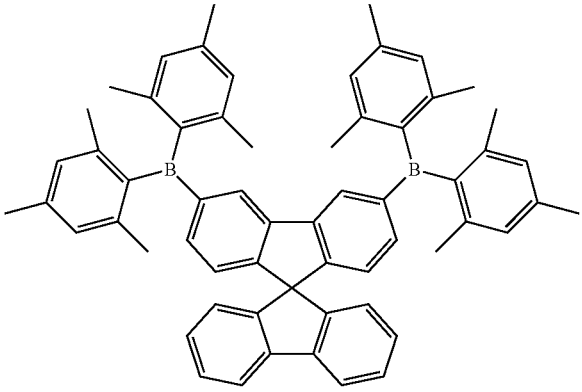 436-59-9 | 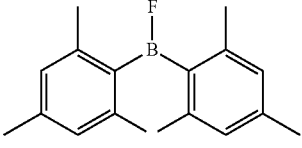 | 34% |
| B9 | 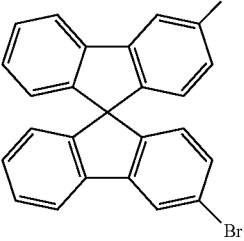 1418299-838 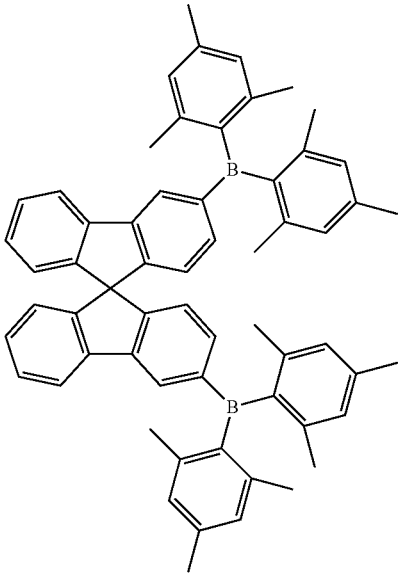 [SMILES: Cc1cc(C)c(B(c2ccc3c(c2)-c2ccccc2C32c3ccccc3-c3cc(B(c4c(C)cc(C)cc4C)c4c(C)cc(C)cc4C)ccc32)c2c(C)cc(C)cc2C)c(C)c1] 436-59-9 | 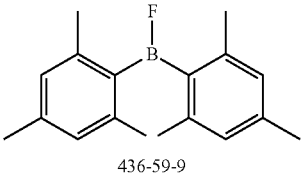 | 31% |
| B10 | 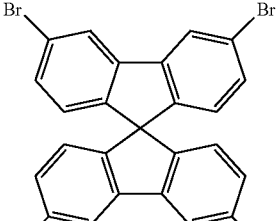 1374997-47-3 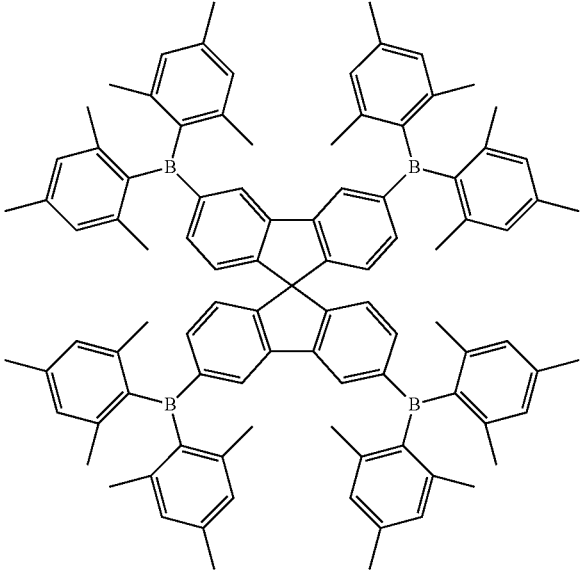 436-59-9 | 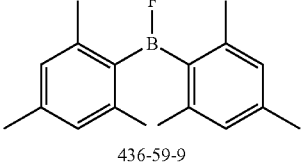 | 29% |

-continued
| Ex. | Reactant | Product | Yield |
|---|---|---|---|
| B11 | 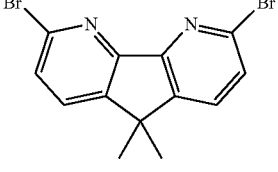
103679-39-1
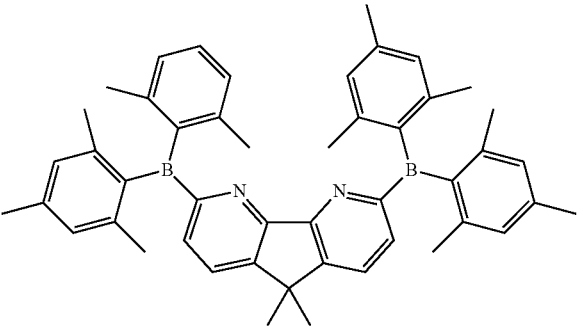
436-59-9 | 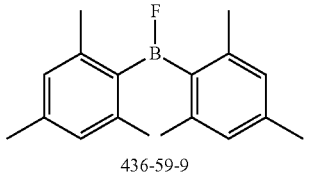 | 32% |
| B12 | 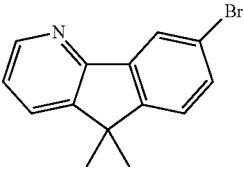
1033894-02-8
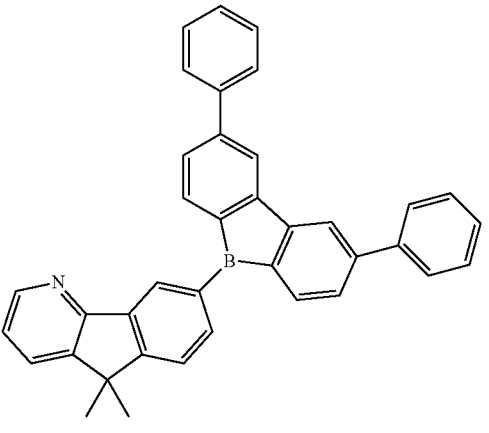 [SMILES: CC1(C)c2ccc(B3c4ccc(-c5ccccc5)cc4-c4cc(-c5ccccc5)ccc43)cc2-c2ncccc21]
1361252-26-7 | 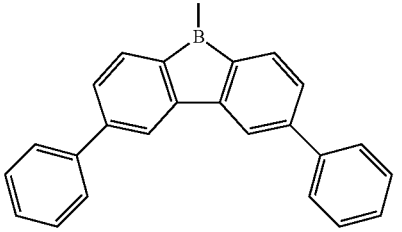 | 25% |
4-Fluorene type
| B13 | 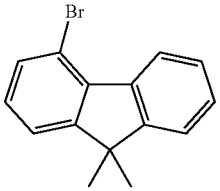
942615-32-9
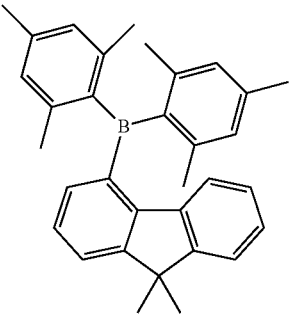
436-59-9 | 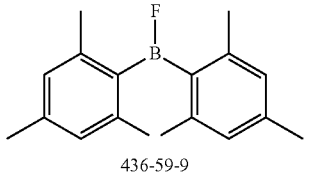 | 27% |

| Ex. | Reactant | Product | Yield |
|---|---|---|---|
| B14 | 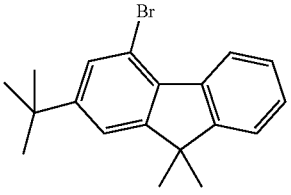 1013652-96-4 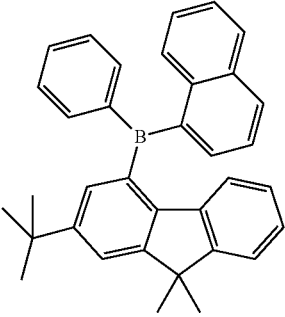 [SMILES: CC(C)(C)c1cc(B(c2ccccc2)c2cccc3ccccc23)c2c(c1)C(C)(C)c1ccccc1-2] 1361247-91-7 | 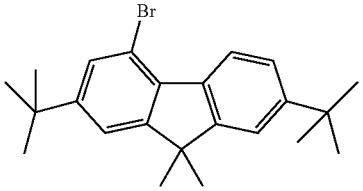 | 24% |
| B15 | 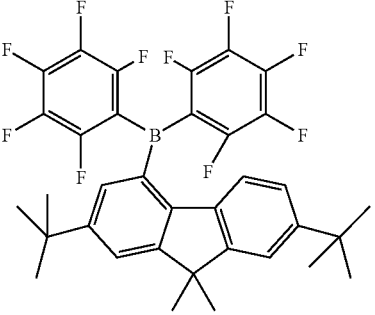 [SMILES: CC(C)(C)c1ccc2c(c1)C(C)(C)c1cc(C(C)(C)C)cc(B(c3c(F)c(F)c(F)c(F)c3F)c3c(F)c(F)c(F)c(F)c3F)c1-2] 942615-28-3 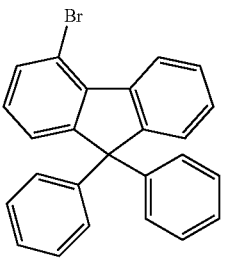 123168-21-8 | 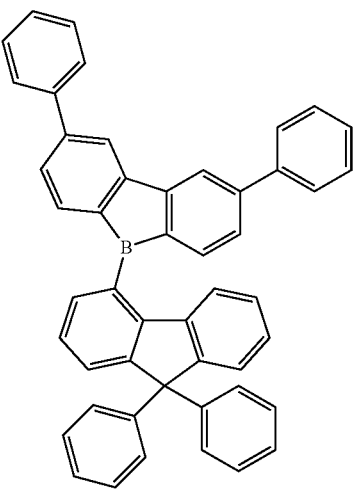 [SMILES: c1ccc(-c2ccc3c(c2)-c2cc(-c4ccccc4)ccc2B3c2cccc3c2-c2ccccc2C3(c2ccccc2)c2ccccc2)cc1] | 23% |
| B16 | 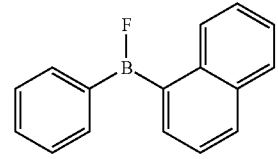 713125-22-5 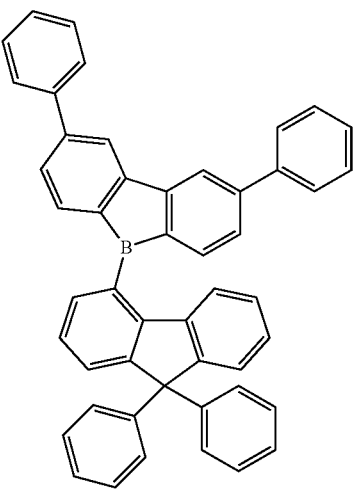 [SMILES: c1ccc(-c2ccc3c(c2)-c2cc(-c4ccccc4)ccc2B3c2cccc3c2-c2ccccc2C3(c2ccccc2)c2ccccc2)cc1] 1361252-26-7 | 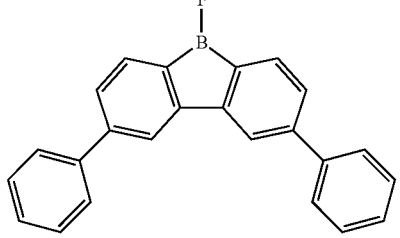 | 25% |

| Ex. | Reactant | Product | Yield |
|---|---|---|---|
| B17 | 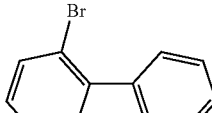 1161009-88-6 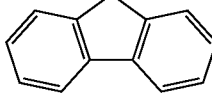 118513-79-4 | 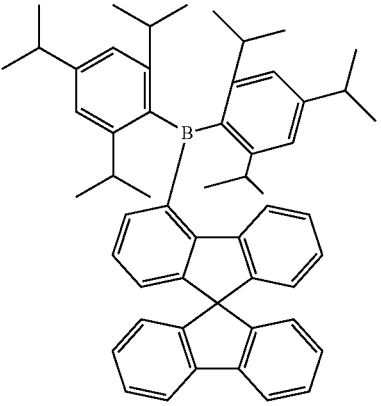 [SMILES: CC(C)c1cc(C(C)C)c(B(c2cccc3c2-c2ccccc2C32c3ccccc3-c3ccccc32)c2c(C(C)C)cc(C(C)C)cc2C(C)C)c(C(C)C)c1] | 19% |
| B18 | 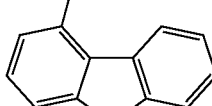 1365480-13-2 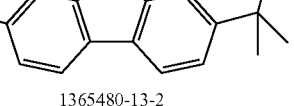 436-59-9 | 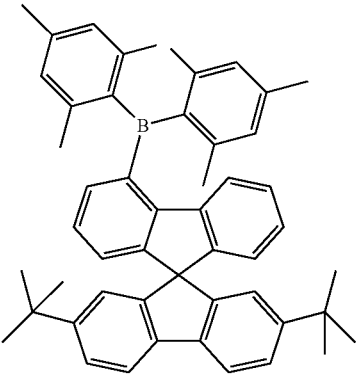 [SMILES: Cc1cc(C)c(B(c2cccc3c2-c2ccccc2C32c3cc(C(C)(C)C)ccc3-c3ccc(C(C)(C)C)cc32)c2c(C)cc(C)cc2C)c(C)c1] | 33% |
| B19 | 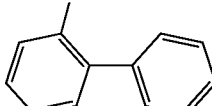 1257321-41-7 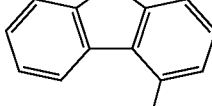 436-59-9 | 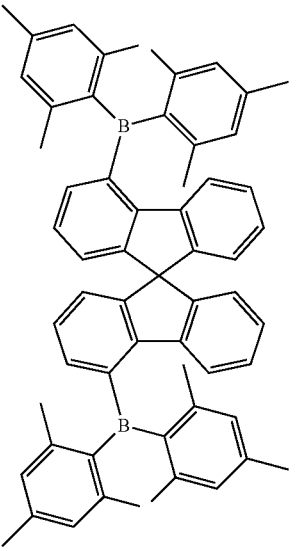 | 29% |

| Ex. | Reactant | Product | Yield |
|---|---|---|---|
| B20 | 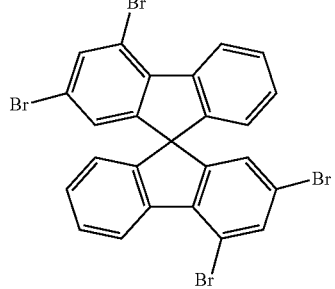<br>171408-83-6<br>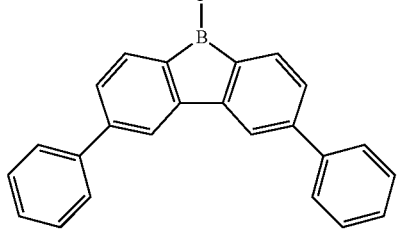<br>1361252-26-7 | 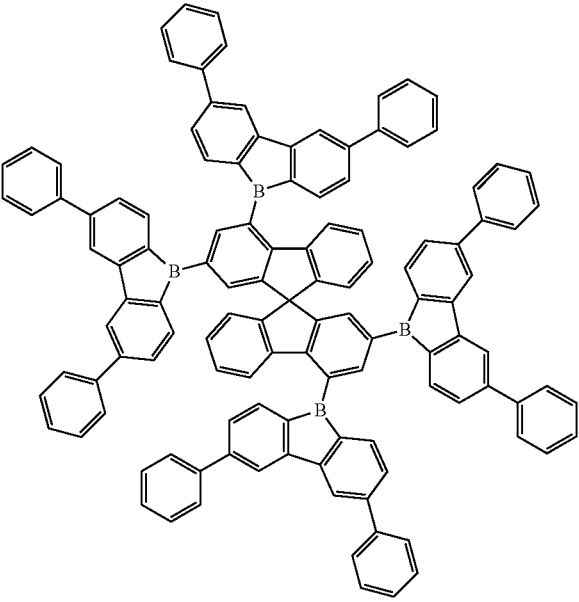 [SMILES: c1ccc(-c2ccc3c(c2)-c2cc(-c4ccccc4)ccc2B3c2cc(B3c4ccc(-c5ccccc5)cc4-c4cc(-c5ccccc5)ccc43)c3c(c2)C2(c4ccccc4-3)c3ccccc3-c3c(B4c5ccc(-c6ccccc6)cc5-c5cc(-c6ccccc6)ccc54)cc(B4c5ccc(-c6ccccc6)cc5-c5cc(-c6ccccc6)ccc54)cc32)cc1] | 25% |
2-Xanthene type
| Ex. | Reactant | Product | Yield |
|---|---|---|---|
| B21 | 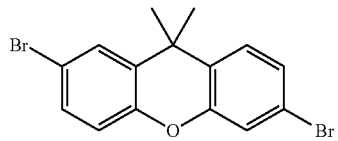<br>1246661-45-9<br>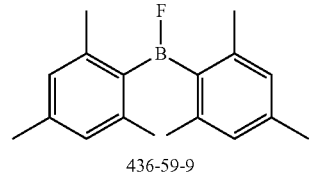<br>436-59-9 | 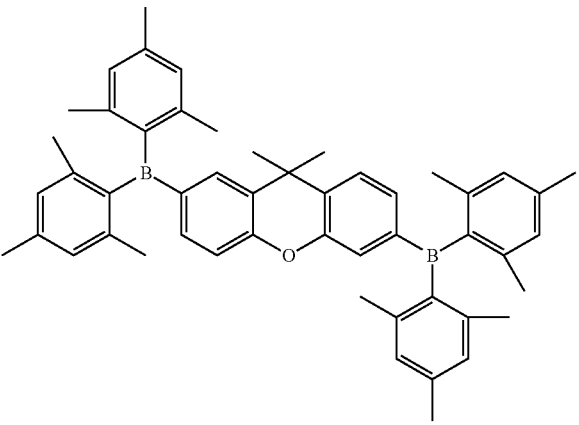 | 36% |
4-Xanthene type
| Ex. | Reactant | Product | Yield |
|---|---|---|---|
| B22 | 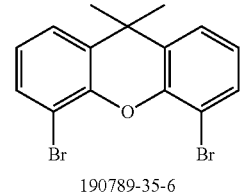<br>190789-35-6<br>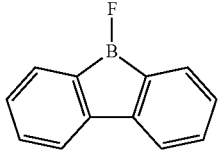<br>119615-28-0 | 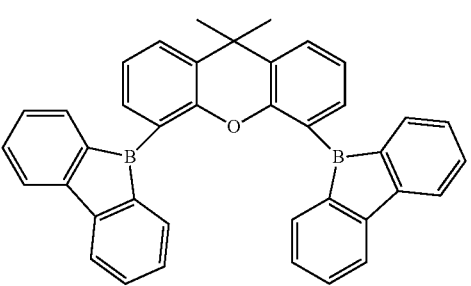 [SMILES: CC1(C)c2cccc(B3c4ccccc4-c4ccccc43)c2Oc2c(B3c4ccccc4-c4ccccc43)cccc21] | 21% |

-continued
| Ex. | Reactant | Product | Yield |
|---|---|---|---|
| B23 | 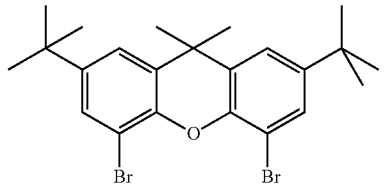<br>130252-43-8<br>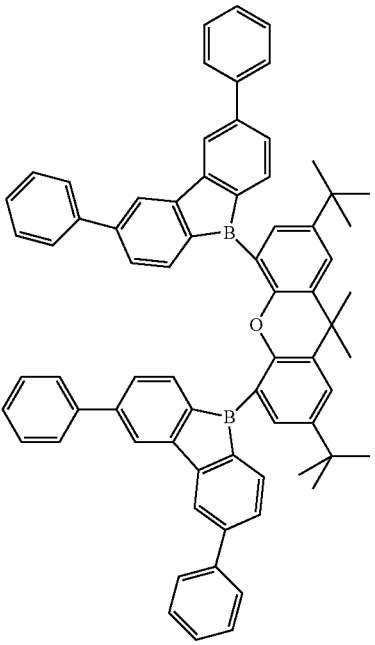 [SMILES: CC(C)(C)c1cc(B2c3ccc(-c4ccccc4)cc3-c3cc(-c4ccccc4)ccc32)c2c(c1)C(C)(C)c1cc(C(C)(C)C)cc(B3c4ccc(-c5ccccc5)cc4-c4cc(-c5ccccc5)ccc43)c1O2]<br>1361252-26-7 | 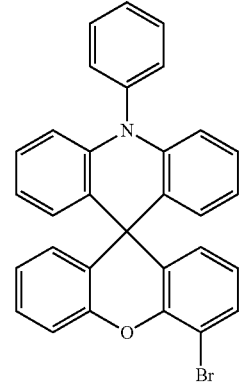 | 23% |
| B24 | 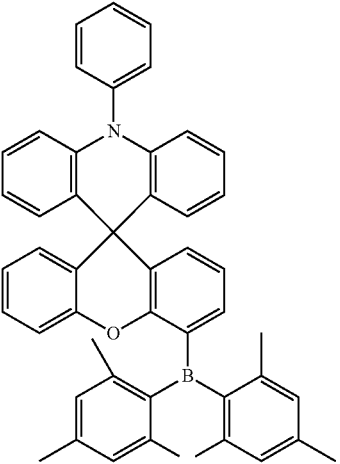 [SMILES: Cc1cc(C)c(B(c2cccc3c2Oc2ccccc2C32c3ccccc3N(c3ccccc3)c3ccccc32)c2c(C)cc(C)cc2C)c(C)c1]<br>1443131-81-1<br><br>436-59-9 | | 35% |

Variant 2

A mixture of 100 mmol of the bromide, 110 mmol of the boronic acid, 300 mmol of sodium hydrogencarbonate, 2 mmol of S-Phos, 1 mmol of palladium(II) acetate, 300 mL of toluene, 200 mL of dioxane and 300 mL of water is heated under reflux for 16 h. After cooling, the aqueous phase is removed, the organic phase is washed three times with 300 mL each time of water and once with 300 mL of sodium chloride solution and dried over magnesium sulfate, and a desiccant is filtered off using a Celite bed. The residue obtained after removal of the solvent is purified by repeated recrystallization (for example from toluene, acetone, ethyl acetate in combination with alcohols such as methanol, ethanol, isopropanol, etc.) and final fractional sublimation twice under high vacuum (p about $10^{-5}$ to $10^{-6}$ mbar, T about 250-400° C.).

Example B25

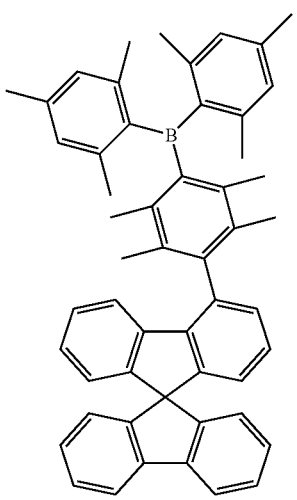

46.1 g (100 mmol) of (4-bromo-2,3,5,6-tetramethylphenyl)bis(2,4,6-trimethylphenyl)borane [321735-74-4], 39.6 g (110 mmol) of spiro-9,9'-bifluorene-4-boronic acid [1421789-05-0], 25.2 g (300 mmol) of sodium hydrogencarbonate, 821 mg (2 mmol) of S-Phos and 249 mg (1 mmol) of palladium(II) acetate. Recrystallization five times from toluene/EtOH. Fractional sublimation twice: p about $10^{-5}$ mbar, T=330-340° C. Yield: 20.2 g (29 mmol), 29%. Purity: 99.9% by HPLC.

In an analogous manner, it is possible to prepare the following compounds:

| Ex. | Reactant | Product | Yield |
|---|---|---|---|
| | | 1-Fluorene type | |
| B26 | 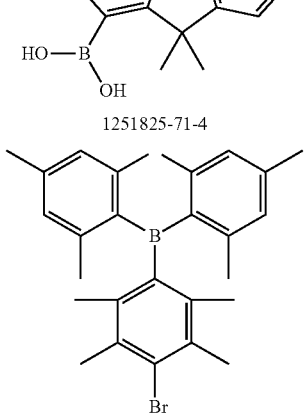 1251825-71-4 <br> 321735-74-4 | 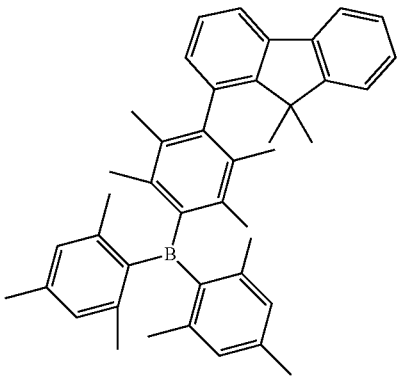 [SMILES: Cc1cc(C)c(B(c2c(C)cc(C)cc2C)c2c(C)c(C)c(-c3cccc4c3C(C)(C)c3ccccc3-4)c(C)c2C)c(C)c1] | 23% |

-continued

| Ex. | Reactant | Product | Yield |
|---|---|---|---|
| B27 | 1251773-34-8<br>1279129-77-9 | | 19% |
| B28 | 1421789-05-0<br>1299485-40-7 | | 21% |

Production of the OLEDs

1) Vacuum-Processed Devices

OLEDs of the invention and OLEDs according to the prior art are produced by a general method according to WO 2004/058911, which is adapted to the circumstances described here (variation in layer thickness, materials used).

In the examples which follow, the results for various OLEDs are presented. Glass plaques with structured ITO (indium tin oxide) form the substrates to which the OLEDs are applied. The OLEDs basically have the following layer structure: substrate/hole transport layer 1 (HTL1) consisting of HTM doped with 3% NDP-9 (commercially available from Novaled), 20 nm/hole transport layer 2 (HTL2)/optional hole transport layer 3 (HTL3)/emission layer (EML)/optional hole blocker layer (HBL)/electron transport layer (ETL)/optional electron injection layer (EIL) and finally a cathode. The cathode is formed by an aluminum layer of thickness 100 nm.

First of all, vacuum-processed OLEDs are described. For this purpose, all the materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as M3:M2:Ir dopant (55%:35%:10%) mean here that the material M3 is present in the layer in a proportion by volume of 55%, M2 in a proportion of 35% and Ir dopant in a proportion of 10%.

Analogously, the electron transport layer may also consist of a mixture of two materials. The exact structure of the OLEDs can be found in Table 1. The materials used for production of the OLEDs are shown in Table 4.

The OLEDs are characterized in a standard manner. For this purpose, the electroluminescence spectra, the power efficiency (measured in cd/A) and the voltage (measured at 1000 cd/m² in V) are determined from current-voltage-brightness characteristics (IUL characteristics). For selected experiments, the lifetime is determined. The lifetime is defined as the time after which the luminance has fallen from a particular starting luminance to a certain proportion. The figure LD50 means that the lifetime specified is the time at which the luminance has dropped to 50% of the starting luminance, i.e. from, for example, 1000 cd/m² to 500 cd/m². According to the emission color, different starting brightnesses were selected. The values for the lifetime can be converted to a figure for other starting luminances with the aid of conversion formulae known to those skilled in the art. In this context, the lifetime for a starting luminance of 1000 cd/m² is a standard figure.

Use of Compounds of the Invention OLEDs

The uses of the compounds of the invention include uses as TMM, ETM and HBM in fluorescent and phosphorescent OLEDs.

TABLE 1

Structure of the OLED

| Ex. | HTL2 thickness | HTL3 thickness | EML thickness | HBL thickness | ETL thickness |
|---|---|---|---|---|---|
| Use as TMM | | | | | |
| Triplet red | | | | | |
| D1 | HTM 240 nm | — | B5:M2:Ir-R (60%:30%:10%) 30 nm | — | ETM1:ETM2 (50%:50%) 20 nm |
| D2 | HTM 240 nm | — | B24:Ir-R (95%:5%) 30 nm | — | ETM1:ETM2 (50%:50%) 20 nm |
| Triplet green | | | | | |
| D3 | HTM 220 nm | — | B1:M2:Ir-G (65%:30%:5%) 25 nm | M1 10 nm | ETM1:ETM2 (50%:50%) 20 nm |
| D4 | HTM 220 nm | — | B7:M2:Ir-G (65%:30%:5%) 25 nm | M1 10 nm | ETM1:ETM2 (50%:50%) 20 nm |
| D5 | HTM 220 nm | — | B9:M2:Ir-G (65%:30%:5%) 25 nm | M1 10 nm | ETM1:ETM2 (50%:50%) 20 nm |
| D6 | HTM 220 nm | — | B11:M2:Ir-G (45%:45%:10%) 25 nm | M1 10 nm | ETM1:ETM2 (50%:50%) 20 nm |
| D7 | HTM 220 nm | — | B18:M2:Ir-G (65%:30%:5%) 25 nm | M1 10 nm | ETM1:ETM2 (50%:50%) 20 nm |
| D8 | HTM 220 nm | — | B21:M2:Ir-G (50%:40%:10%) 25 nm | M1 10 nm | ETM1:ETM2 (50%:50%) 20 nm |
| D9 | HTM 220 nm | — | B25:M2:Ir-G (50%:40%:10%) 25 nm | M1 10 nm | ETM1:ETM2 (50%:50%) 20 nm |
| D10 | HTM 220 nm | — | B28:M2:Ir-G (60%:30%:10%) 25 nm | M1 10 nm | ETM1:ETM2 (50%:50%) 20 nm |
| Comp. 1 | HTM 220 nm | — | Ref. 1:M2:Ir-G (60%:30%:10%) 25 nm | M1 10 nm | ETM1:ETM2 (50%:50%) 20 nm |
| Triplet blue | | | | | |
| D11 | HTM 200 nm | EBM 10 nm | B8:M3:Ir-B (50%:40%:10%) 25 nm | M1 10 nm | ETM1:ETM2 (50%:50%) 20 nm |
| D12 | HTM 200 nm | EBM 10 nm | B19:M3:Ir-B (40%:50%:10%) 25 nm | M1 10 nm | ETM1:ETM2 (50%:50%) 20 nm |
| Comp. 2 | HTM 200 nm | EBM 10 nm | Ref. 1:M3:Ir-B (40%:50%:10%) 25 nm | M1 10 nm | ETM1:ETM2 (50%:50%) 20 nm |

TABLE 1-continued

| | | Structure of the OLED | | | |
|---|---|---|---|---|---|
| Ex. | HTL2 thickness | HTL3 thickness | EML thickness | HBL thickness | ETL thickness |
| | | Use as ETM/HBM | | | |
| | | Triplet green | | | |
| D13 | HTM 220 nm | — | M1:M2:Ir-G (65%:30%:5%) 25 nm | — | B25 (100%) 30 nm/ ETM2 2 nm |
| D14 | HTM 220 nm | — | B16:M2:Ir-G (45%:45%:10%) 25 nm | B16 10 nm | B23 (100%) 20 nm/ ETM2 2 nm |
| | | Singlet blue | | | |
| D15 | HTM 190 nm | — | SMB:SEB (95%:5%) 25 nm | — | B11 (100%) 20 nm/ ETM2 2 nm |
| D16 | HTM 190 nm | — | SMB:SEB (95%:5%) 25 nm | — | B14 (100%) 20 nm/ ETM2 2 nm |
| Comp. 3 | HTM 190 nm | — | SMB:SEB (95%:5%) 25 nm | — | Ref. 2 (100%) 20 nm/ ETM2 2 nm |

TABLE 2

| | Results for the vacuum processed OLEDs | | | |
|---|---|---|---|---|
| Ex. | EQE (%) 1000 cd/m$^2$ | Voltage (V) 1000 cd/m$^2$ | CIE x/y 1000 cd/m$^2$ | LD50 (h) 1000 cd/m$^2$ |
| | | Use as TMM | | |
| | | Triplet red | | |
| D1 | 13.7 | 3.7 | 0.66/0.33 | — |
| D2 | 14.3 | 3.2 | 0.66/0.33 | 85000 |
| | | Triplet green | | |
| D3 | 19.0 | 4.0 | 0.34/0.63 | — |
| D4 | 18.7 | 4.0 | 0.35/0.62 | — |
| D5 | 18.8 | 4.2 | 0.34/0.63 | — |
| D6 | 20.4 | 3.3 | 0.35/0.63 | 70000 |
| D7 | 18.3 | 4.2 | 0.35/0.62 | — |
| D8 | 18.5 | 4.1 | 0.35/0.62 | — |
| D9 | 19.3 | 4.3 | 0.35/0.64 | — |
| D10 | 18.8 | 4.0 | 0.34/0.62 | 55000 |
| Comp. 1 | 16.6 | 4.4 | 0.34/0.63 | 35000 |
| | | Triplet blue | | |
| D11 | 12.5 | 3.8 | 0.15/0.31 | — |
| D12 | 13.2 | 4.0 | 0.15/0.30 | — |
| Comp. 2 | 10.4 | 4.0 | 0.15/0.33 | — |
| | | Use as ETM/HBM | | |
| | | Triplet green | | |
| D13 | 19.3 | 3.6 | 0.34/0.62 | 45000 |
| D14 | 20.1 | 3.7 | 0.35/0.62 | — |
| | | Singlet blue | | |
| D15 | 8.5 | 4.0 | 0.15/0.17 | — |
| D16 | 8.1 | 4.8 | 0.15/0.17 | 12000 |
| Comp. 3 | 7.2 | 4.3 | 0.15/0.17 | 7500 |

2) Solution-Processed Devices

A: From Soluble Functional Materials

The compounds of the invention may also be processed from solution and in that case lead to OLEDs which are much simpler in terms of process technology compared to the vacuum-processed OLEDs, but nevertheless have good properties. The production of such components is based on the production of polymeric light-emitting diodes (PLEDs), which has already been described many times in the literature (for example in WO 2004/037887).

The structure is composed of substrate/ITO/PEDOT (80 nm)/interlayer (80 nm)/emission layer (80 nm)/cathode. For this purpose, substrates from Technoprint (soda-lime glass) are used, to which the ITO structure (indium tin oxide, a transparent conductive anode) is applied. The substrates are cleaned in a cleanroom with DI water and a detergent (Deconex 15 PF) and then activated by a UV/ozone plasma treatment. Thereafter, likewise in the cleanroom, as a buffer layer, an 80 nm layer of PEDOT (PEDOT is a polythiophene derivative (Baytron P VAI 4083sp.) from H. C. Starck, Goslar, which is supplied as an aqueous dispersion) is applied by spin-coating. The required spin rate depends on the degree of dilution and the specific spin-coater geometry (typical value for 80 nm: 4500 rpm). In order to remove residual water from the layer, the substrates are baked on a hotplate at 180° C. for 10 minutes. The interlayer used serves for hole injection; in this case, HIL-012 from Merck is used. The interlayer may alternatively also be replaced by one or more layers which merely have to fulfill the condition of not being leached off again by the subsequent processing step of EML deposition from solution. For production of the emission layer, the emitters of the invention are dissolved together with the matrix materials in toluene. The typical solids content of such solutions is between 16 and 25 g/l when, as here, the layer thickness of 80 nm which is typical of a device is to be achieved by means of spin-coating. The solution-processed devices contain an emission layer composed of (polystyrene):matrix1:matrix2:Ir-G-Sol (25%: 35%:20%:20%). The emission layer is spun on in an inert gas atmosphere, argon in the present case, and baked at 130° C. for 30 min. Lastly, a cathode composed of barium (5 nm) and then aluminum (100 nm) (high-purity metals from Aldrich, particularly barium 99.99% (cat. no. 474711); vapor deposition systems from Lesker or the like, typical vapor deposition pressure $5\times10^{-6}$ mbar) is applied by vapor deposition. It is optionally possible first to apply a hole blocker layer and then an electron transport layer and only then the cathode (e.g. Al or LiF/Al) by vapor deposition under reduced pressure. In order to protect the device from air and air humidity, the device is finally encapsulated and then characterized. The OLED examples cited are yet to be optimized; Table 3 summarizes the data obtained.

TABLE 3

Results with materials processed from solution

| Ex. | Matrix1 Matrix2 | EQE (%) 1000 cd/m$^2$ | Voltage (V) 1000 cd/m$^2$ | CIE x/y 1000 cd/m$^2$ |
|---|---|---|---|---|
| | | Green OLEDs | | |
| D-Sol1 | B10 M4 | 17.8 | 5.8 | 0.34/0.64 |
| D-Sol1 | B20 M4 | 18.5 | 5.6 | 0.35/0.63 |

TABLE 4

Structural formulae of the materials used

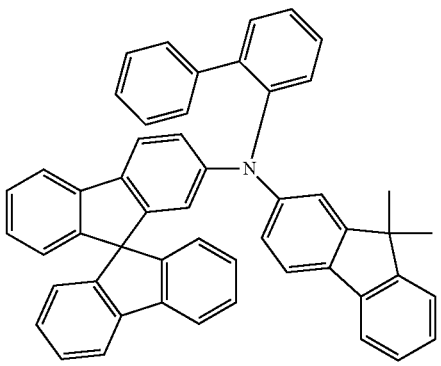 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

HTM

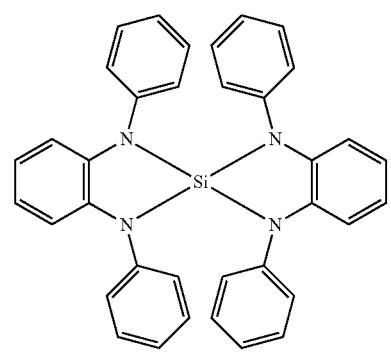 [SMILES: c1ccc(N2c3ccccc3N(c3ccccc3)[Si]23N(c2ccccc2)c2ccccc2N3c2ccccc2)cc1]

EBM

TABLE 4-continued
Structural formulae of the materials used
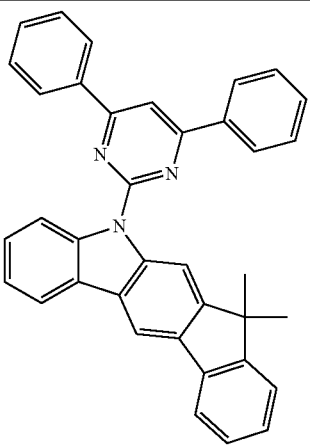
M1
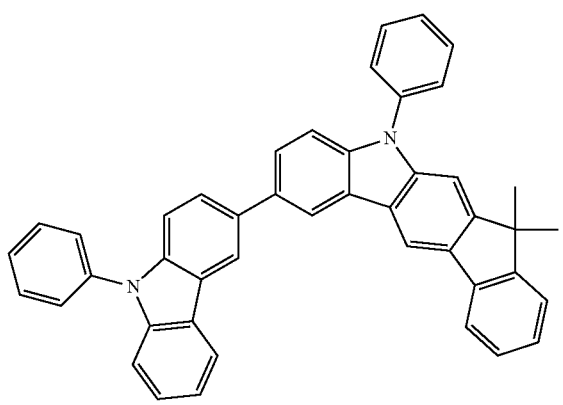 [SMILES: CC1(C)c2ccccc2-c2cc3c4cc(-c5ccc6c(c5)c5ccccc5n6-c5ccccc5)ccc4n(-c4ccccc4)c3cc21]
M2
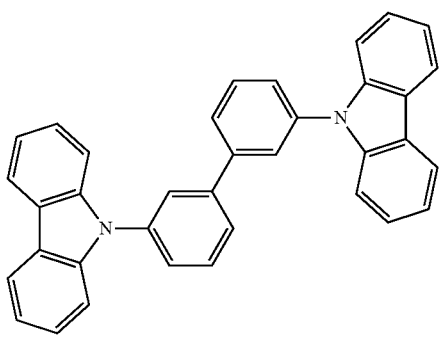 [SMILES: c1cc(-c2cccc(-n3c4ccccc4c4ccccc43)c2)cc(-n2c3ccccc3c3ccccc32)c1]
M3
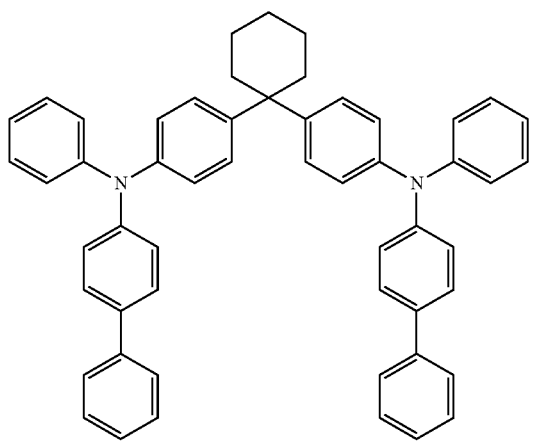 [SMILES: c1ccc(-c2ccc(N(c3ccccc3)c3ccc(C4(c5ccc(N(c6ccccc6)c6ccc(-c7ccccc7)cc6)cc5)CCCCC4)cc3)cc2)cc1]
M4

TABLE 4-continued
Structural formulae of the materials used
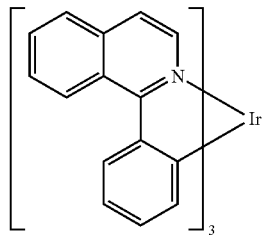
Ir-R
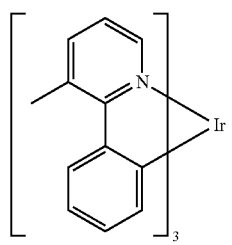
Ir-G
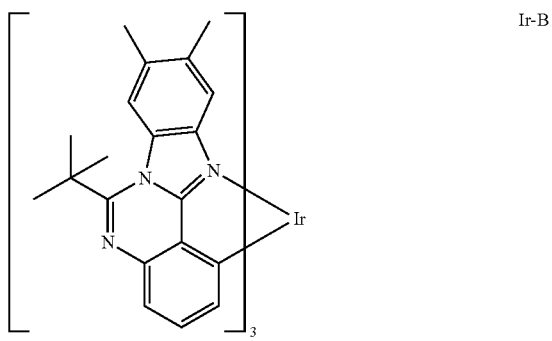
Ir-B
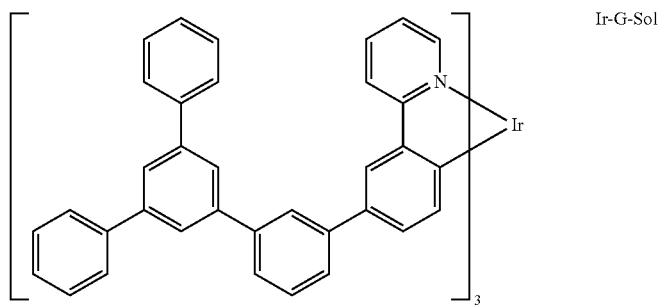
Ir-G-Sol TABLE 4-continued
Structural formulae of the materials used
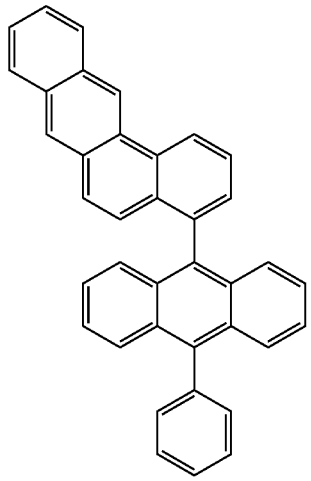 [SMILES: c1ccc(-c2c3ccccc3c(-c3cccc4c3ccc3cc5ccccc5cc34)c3ccccc23)cc1]
SBM
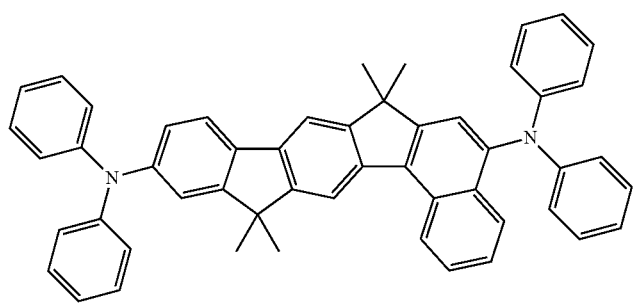 [SMILES: CC1(C)c2cc(N(c3ccccc3)c3ccccc3)ccc2-c2cc3c(cc21)-c1c(cc(N(c2ccccc2)c2ccccc2)c2ccccc12)C3(C)C]
SEB
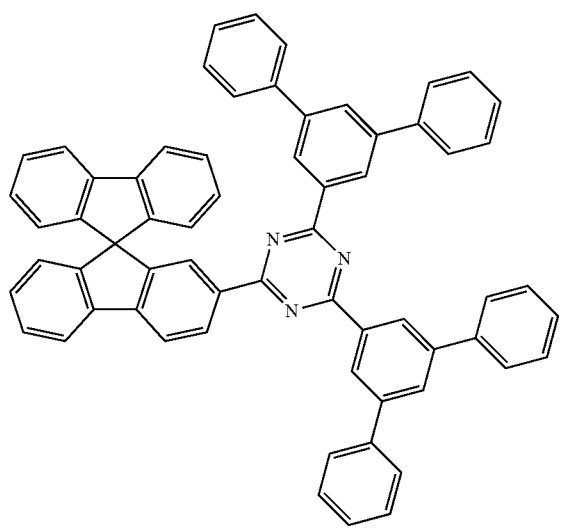 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ETM1

TABLE 4-continued

Structural formulae of the materials used

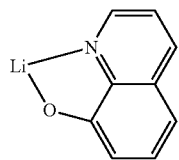

ETM2

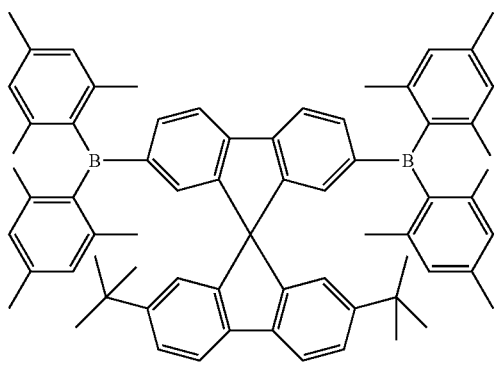

Ref. 1

EP 1 345948 B1

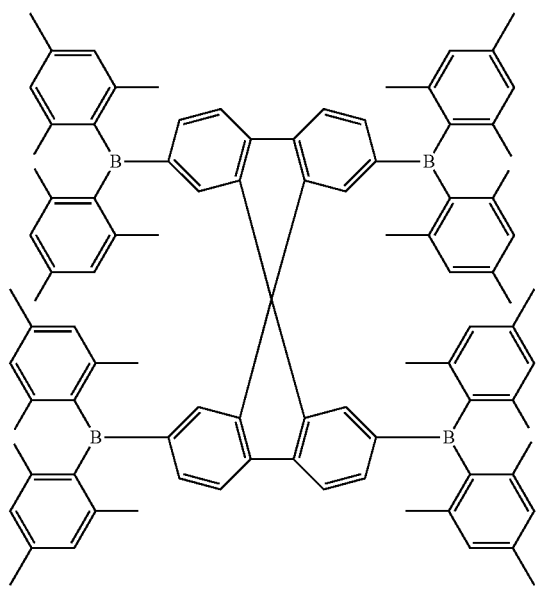

Ref. 2

EP 1 345948 B1

Determination of the HOMO/LUMO Positions and the Triplet Level

The triplet level $T_1$ of the compounds is determined via quantum-chemical calculations. For this purpose, the "Gaussian03 W" (Gaussian Inc.) software package is used. For calculation of organic substances, an optimization of geometry is first conducted by the "Ground State/Semi-empirical/Default Spin/AM1" (charge 0/spin singlet) method. Subsequently, an energy calculation is effected on the basis of the optimized geometry. This is done using the "TD-SCF/DFT/Default Spin/B3PW91" method with the "6-31G(d)" basis set (charge 0/spin singlet). The energy calculation gives the energy of the T1 state in eV which is reported for the two compounds Ref. 1 and Ex. 18 in table 1.

TABLE 1

Calculated triplet energy

| Substance | Triplet energy [eV] |
|---|---|
| Ref. 1 from EP 1 345948 B1 | 2.56 |
| B 18 | 2.80 |

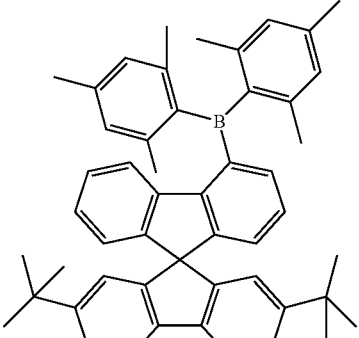

B 18

The data show that triplet level can surprisingly be raised by the measures of the invention as compared with the prior art.

The invention claimed is:

1. A boron-containing compound comprising at least one structure of the formulae (I) and/or (V)

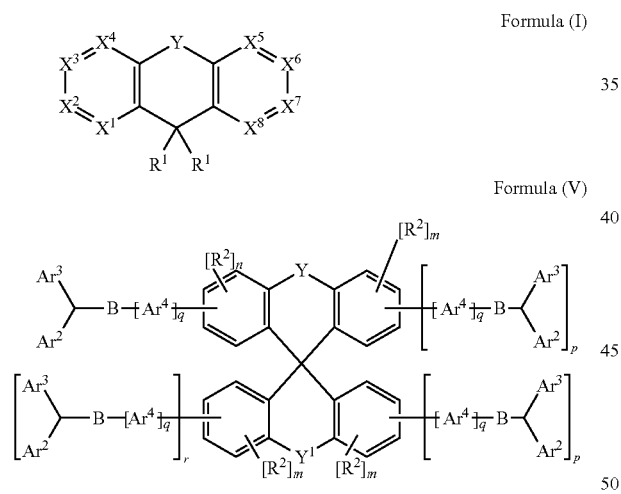

Formula (I)

Formula (V)

where the symbols used are as follows:

$X^1$, $X^2$, $X^3$, $X^4$, $X^5$, $X^6$, $X^7$, $X^8$
is the same or different at each instance and is N, $CR^2$ or C—Z, where exactly one of the $X^1$, $X^2$, $X^3$, $X^4$, $X^5$, $X^6$, $X^7$, $X^8$, groups is C—Z and no two adjacent $X^1$, $X^2$, $X^3$, $X^4$, $X^5$, $X^6$, $X^7$, $X^8$, groups are simultaneously N;

Y, $Y^1$ is the same or different at each instance and is a bond or a bivalent bridge selected from $BR^3$, O, S, $C(R^3)_2$, $C(R^3)=C(R^3)$, $N(R^3)$, $Si(R^3)_2$, C=O, C=C$(R^3)_2$, S=O, $SO_2$, $C(R^3)_2$—$C(R^3)_2$, and 1,2-phenylene;

$R^1$ is the same or different at each instance and is H, D, F, Cl, Br, I, CHO, C(=O)$Ar^1$, P(=O)($Ar^1$)$_2$, S(=O)$Ar^1$, S(=O)$_2Ar^1$, CN, $NO_2$, $Si(R^4)_3$, $B(OR^4)_2$, $OSO_2R^4$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^4$ radicals, where one or more nonadjacent $CH_2$ groups may be replaced by $R^4C$=$CR^4$, C≡C, $Si(R^4)_2$, $Ge(R^4)_2$, $Sn(R^4)_2$, C=O, C=S, C=Se, P(=O)($R^4$), SO, $SO_2$, O, S or $CONR^4$ and where one or more hydrogen atoms may be replaced by D, F, Cl, Br, I, CN or $NO_2$, or an aromatic or heteroaromatic ring system which has 5 to 40 aromatic ring atoms, each of which may be substituted by one or more $R^4$ radicals, or an aryloxy or heteroaryloxy group which has 5 to 40 aromatic ring atoms and may be substituted by one or more $R^4$ radicals, or a combination of these systems; at the same time;

$R^2$, $R^3$ is the same or different at each instance and is H, D, F, Cl, Br, I, CHO, C(=O)$Ar^1$, P(=O)($Ar^1$)$_2$, S(=O)$Ar^1$, S(=O)$_2Ar^1$, CN, $NO_2$, $Si(R^4)_3$, $B(OR^4)_2$, $OSO_2R^4$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^4$ radicals, where one or more nonadjacent $CH_2$ groups may be replaced by $R^4C$=$CR^4$, C≡C, $Si(R^4)_2$, $Ge(R^4)_2$, $Sn(R^4)_2$, C=O, C=S, C=Se, P(=O)($R^4$), SO, $SO_2$, O, S or $CONR^4$ and where one or more hydrogen atoms may be replaced by D, F, Cl, Br, I, CN or $NO_2$, or an aromatic or heteroaromatic ring system which has 5 to 40 aromatic ring atoms, each of which may be substituted by one or more $R^4$ radicals, or an aryloxy or heteroaryloxy group which has 5 to 40 aromatic ring atoms and may be substituted by one or more $R^4$ radicals, or a combination of these systems; at the same time, two or more adjacent $R^2$ or $R^3$ substituents may also form a mono- or polycyclic, aliphatic or aromatic ring system with one another;

$R^4$ is the same or different at each instance and is H, D, F, Cl, Br, I, CHO, C(=O)$Ar^1$, P(=O)($Ar^1$)$_2$, S(=O)$Ar^1$, S(=O)$_2Ar^1$, CN, $NO_2$, $Si(R^5)_3$, $B(OR^5)_2$, $OSO_2R^5$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^5$ radicals, where one or more nonadjacent $CH_2$ groups may be replaced by C≡C, $Si(R^5)_2$, $Ge(R^5)_2$, $Sn(R^5)_2$, C=O, C=S, C=Se, P(=O)($R^5$), SO, $SO_2$, O, S or $CONR^5$ and where one or more hydrogen atoms may be replaced by D, F, Cl, Br, I, CN or $NO_2$, or a combination of these systems; at the same time, two or more adjacent $R^4$ substituents may also form a mono- or polycyclic, aliphatic or aromatic ring system with one another;

$Ar^1$ is the same or different at each instance and is an aromatic or heteroaromatic ring system which has 5 to 30 aromatic ring atoms and may be substituted by one or more $R^3$ radicals; at the same time, it is also possible for two $Ar^1$ radicals bonded to the same phosphorus atom to be joined to one another by a single bond or a bridge selected from $B(R^5)$, $C(R^5)_2$, $Si(R^5)_2$, C=O, C=$NR^5$, C=C$(R^5)_2$, O, S, S=O, $SO_2$, $N(R^5)$, $P(R^5)$ and P(=O)$R^5$;

$R^5$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more adjacent $R^5$ substituents together may also form a mono- or polycyclic, aliphatic or aromatic ring system;

Z is a group of the formula (III)

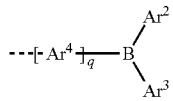

Formula (III)

in which the symbols used are as follows:

$Ar^2$, $Ar^3$ is the same or different at each instance and is an aromatic or heteroaromatic ring system which has 5 to 30 aromatic ring atoms and may be substituted by one or more $R^3$ radicals; at the same time, it is also possible for the $Ar^2$ and $Ar^3$ radicals to be joined to one another by a single bond or a bridge selected from $B(R^5)$, $C(R^5)_2$, $Si(R^5)_2$, C=O, C=$NR^5$, C=$C(R^5)_2$, O, S, S=O, $SO_2$, $N(R^5)$, $P(R^5)$ and P(=O)$R^5$;

q is 0 or 1; and $Ar^4$ is the same or different at each instance and is an aryl group having 6 to 40 carbon atoms or a heteroaryl group having 3 to 40 carbon atoms, each of which may be substituted by one or more $R^3$ radicals; where the dashed line represents the bond of the Z group to the carbon atom of the aromatic or heteroaromatic ring;

p and r are 0;

n and m are the same or different at each instance and are 0 or 1.

2. A compound as claimed in claim 1, wherein not more than two $X^1$, $X^2$, $X^3$, $X^4$, $X^5$, $X^6$, $X^7$, $X^8$, groups are N.

3. A compound as claimed in claim 1, wherein the $X^5$, $X^6$, $X^7$, $X^8$, groups are $CR^2$.

4. A compound as claimed in claim 1, wherein the $X^2$, $X^7$, groups are a group of the formula $CR^2$.

5. A compound as claimed in claim 1, wherein at least two of the $X^2$, $X^7$, groups are a group of the formula C—H.

6. A compound as claimed in claim 1, wherein q is 0, and the boron atom of the Z radical is bonded directly to the fluorene or spiro group.

7. A compound as claimed in claim 1, wherein, in formula (I), at least 4 of the $X^1$, $X^2$, $X^3$, $X^4$, $X^5$, $X^6$, $X^7$ and $X^8$ groups are C—H.

8. A compound as claimed in claim 1, wherein, in formula (I), at least one of the $X^1$, $X^4$, $X^5$ and $X^8$ groups is C—Z.

9. A compound as claimed in claim 1, wherein at least one of the $R^1$ radicals in formula (I) is an alkyl radical having 1 to 10 carbon atoms or an aryl group having 6 to 10 carbon atoms, which may be substituted by up to three $R^4$ radicals.

10. A compound as claimed in claim 1, wherein the compound comprises structures of the formulae (IV) and/or (V)

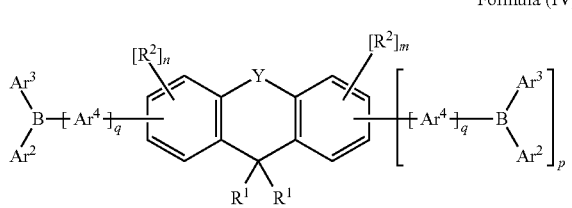

Formula (IV)

11. A compound as claimed in claim 1, wherein the compound comprises structures of the formulae (IV-1) and/or (IV-2)

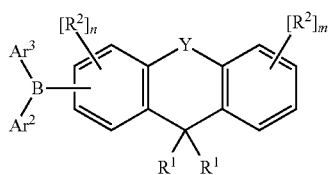

Formula (IV-1)

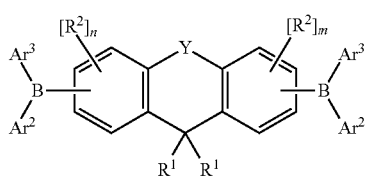

Formula (IV-2)

where n, m are the same or different at each instance and are 0 or 1.

12. A compound as claimed in claim 11, wherein Y is O or a bond.

13. A compound as claimed in claim 1, wherein the compound comprises structures of the formulae (IV-3), (IV-4) and/or (IV-5)

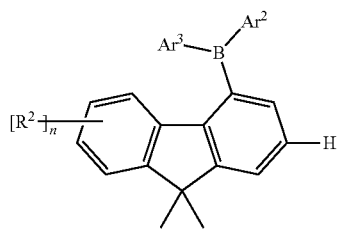

Formula (IV-3)

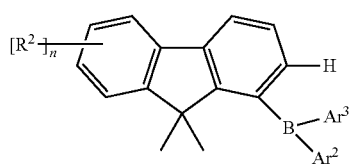

Formula (IV-4)

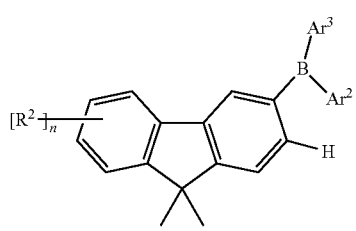

Formula (IV-5)

where n is 0 or 1.

14. A compound as claimed in claim 1, wherein the compound comprises structures of the formulae (IV-6), (IV-7) and/or (IV-8)

Formula (IV-6)

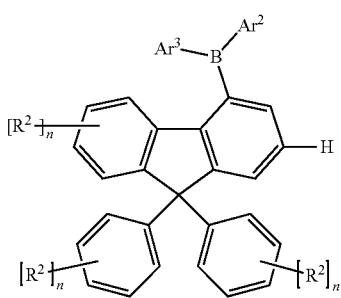

Formula (IV-7)

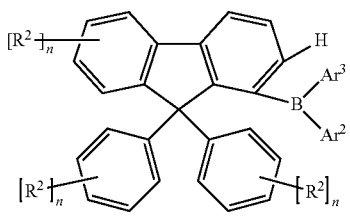

Formula (IV-8)

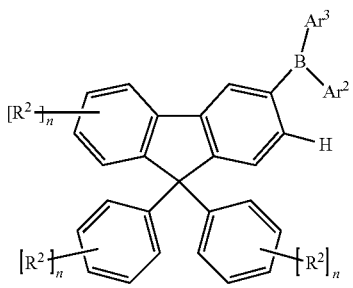

where n is the same or different at each instance and is 0 or 1.

15. A compound as claimed in claim 1, wherein the compound comprises structures of the formula (V-4)

Formula (V-4)

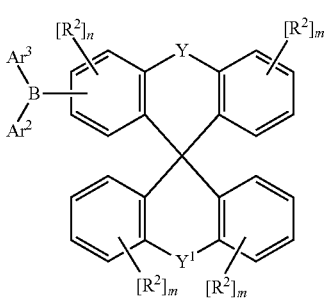

where n, m are the same or different at each instance and are 0 or 1.

16. A compound as claimed in claim 15, wherein Y is O or a bond and $Y^1$ is a bond, O, S, C=O or $N(R^3)$, O or $N(Ar^1)$.

17. A compound as claimed in claim 1, wherein the compound comprises structures of the formulae (V-6), (V-8), and/or (V-10)

Formula (V-6)

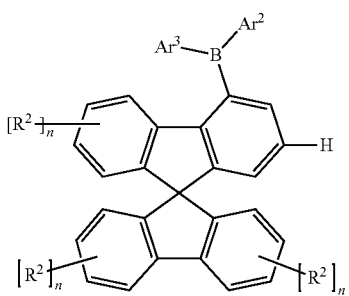

Formula (V-8)

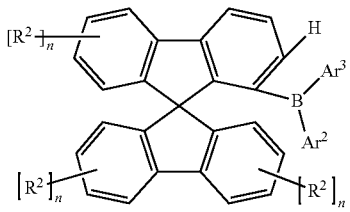

Formula (V-10)

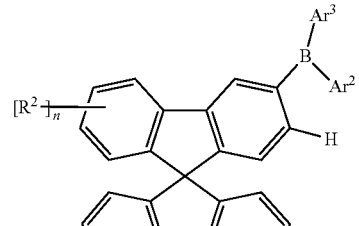

where n is the same or different at each instance and is 0 or 1.

18. A compound as claimed in claim 1, wherein the $Ar^2$ and $Ar^3$ radicals are an aryl group which has 6 carbon atoms and optionally substituted by up to three $R^3$ radicals; at the same time, optionally the $Ar^2$ and $Ar^3$ radicals are joined to one another by a single bond or a bridge selected from $B(R^5)$, $C(R^5)_2$, $Si(R^5)_2$, C=O, C=$NR^5$, C=$C(R^5)_2$, O, S, S=O, $SO_2$, $N(R^5)$, $P(R^5)$ and P(=O)$R^5$.

19. A compound as claimed in claim 1, wherein the compound is an oligomer, polymer or dendrimer.

20. A composition comprising at least one compound as claimed in claim 1 and at least one further compound selected from the group consisting of fluorescent emitters, phosphorescent emitters, host materials, matrix materials, electron transport materials, electron injection materials, hole conductor materials, hole injection materials, electron blocker materials, and hole blocker materials.

21. A formulation comprising at least one compound as claimed in claim 1 and at least one solvent.

22. A process for preparing a compound as claimed in claim 1 comprising reacting at least one aryllithium compound with at least one haloborane and/or at least one borinic ester.

23. An electronic device comprising the compound as claimed in claim 1 as hole blocker material, electron injection material and/or electron transport material.

24. An electronic device comprising at least one compound as claimed in claim 1 wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field-quench devices, light-emitting electrochemical cells, and organic laser diodes.

* * * * *